(12) United States Patent
Adair et al.

(10) Patent No.: US 6,211,904 B1
(45) Date of Patent: Apr. 3, 2001

(54) SURGICAL DEVICES INCORPORATING REDUCED AREA IMAGING DEVICES

(76) Inventors: Edwin L. Adair, 317 Paragon Way, Castle Pines Village, CO (US) 80104; Jeffrey L. Adair, 1861 E. Redfox Pl., Highlands Ranch, CO (US) 80126; Randall S. Adair, 3082 S. Flamingo Way, Denver, CO (US) 80222

( * ) Notice: Subject to any disclaimer, the term of this patent is extended or adjusted under 35 U.S.C. 154(b) by 0 days.

(21) Appl. No.: 09/544,528

(22) Filed: Apr. 6, 2000

Related U.S. Application Data

(63) Continuation-in-part of application No. 09/496,312, filed on Feb. 1, 2000, which is a continuation of application No. 09/175,685, filed on Oct. 20, 1998, now Pat. No. 6,043,839, which is a continuation-in-part of application No. 08/944,322, filed on Oct. 6, 1997, now Pat. No. 5,929,901, and a continuation-in-part of application No. 08/927,785, filed on Sep. 11, 1997, now Pat. No. 6,086,528.

(51) Int. Cl.$^7$ ..................................................... H04N 9/47
(52) U.S. Cl. ................................................ 348/76; 348/65
(58) Field of Search ................................. 348/65, 66, 67, 348/69, 70, 75, 76, 77; 600/109, 110, 160, 172

(56) References Cited

U.S. PATENT DOCUMENTS

| | | | | |
|---|---|---|---|---|
| 5,162,913 | * | 11/1992 | Chatenever et al. | 358/98 |
| 5,471,515 | * | 11/1995 | Fossum et al. | 377/60 |
| 5,734,418 | * | 3/1998 | Danna | 348/76 |
| 5,754,313 | * | 5/1998 | Pelchy et al. | 348/76 |
| 6,106,457 | * | 8/2000 | Perkins et al. | 600/109 |
| 6,139,489 | * | 10/2000 | Wampler et al. | 600/109 |
| 6,141,037 | * | 10/2000 | Upton et al. | 348/65 |

* cited by examiner

Primary Examiner—Andy Rao
(74) Attorney, Agent, or Firm—Sheridan Ross P.C.

(57) ABSTRACT

Configurations of a reduced area imaging device include the image sensor placed remote from the remaining circuitry, or all of the circuitry to include the image sensor placed in a stacked fashion at the same location. The entire imaging device can be placed at the distal tip of an endoscope or within a simple tubular structure, or the image sensor can be remote from the remaining circuitry, wherein a control box which communicates with the image sensor is placed remotely from the image sensor. The imaging device can be incorporated in the housing of a standard medical camera adapted for use with traditional rod lens endoscopes. In any of the configurations, the image sensor may be placed alone on a first circuit board, or timing and control circuits may be included on the first circuit board containing the image sensor. One or more video processing boards can be stacked in a longitudinal fashion with respect to the first board, or the video processing boards may be placed in the control box. The small size of the tubular structure or microendoscope which houses the imaging device allows its use with many surgical instruments which traditionally do not have integral imaging capability such as Jackson grasping forceps; stent placement catheters; balloon catheters; over-tube tissue separating, dissecting or fulgeration devices; modified endotracheal intubation devices or trochars resulting in unique methods of performing surgical tasks by providing imaging capability throughout all stages of introducing and removing the instruments from within the body of a patient.

58 Claims, 17 Drawing Sheets

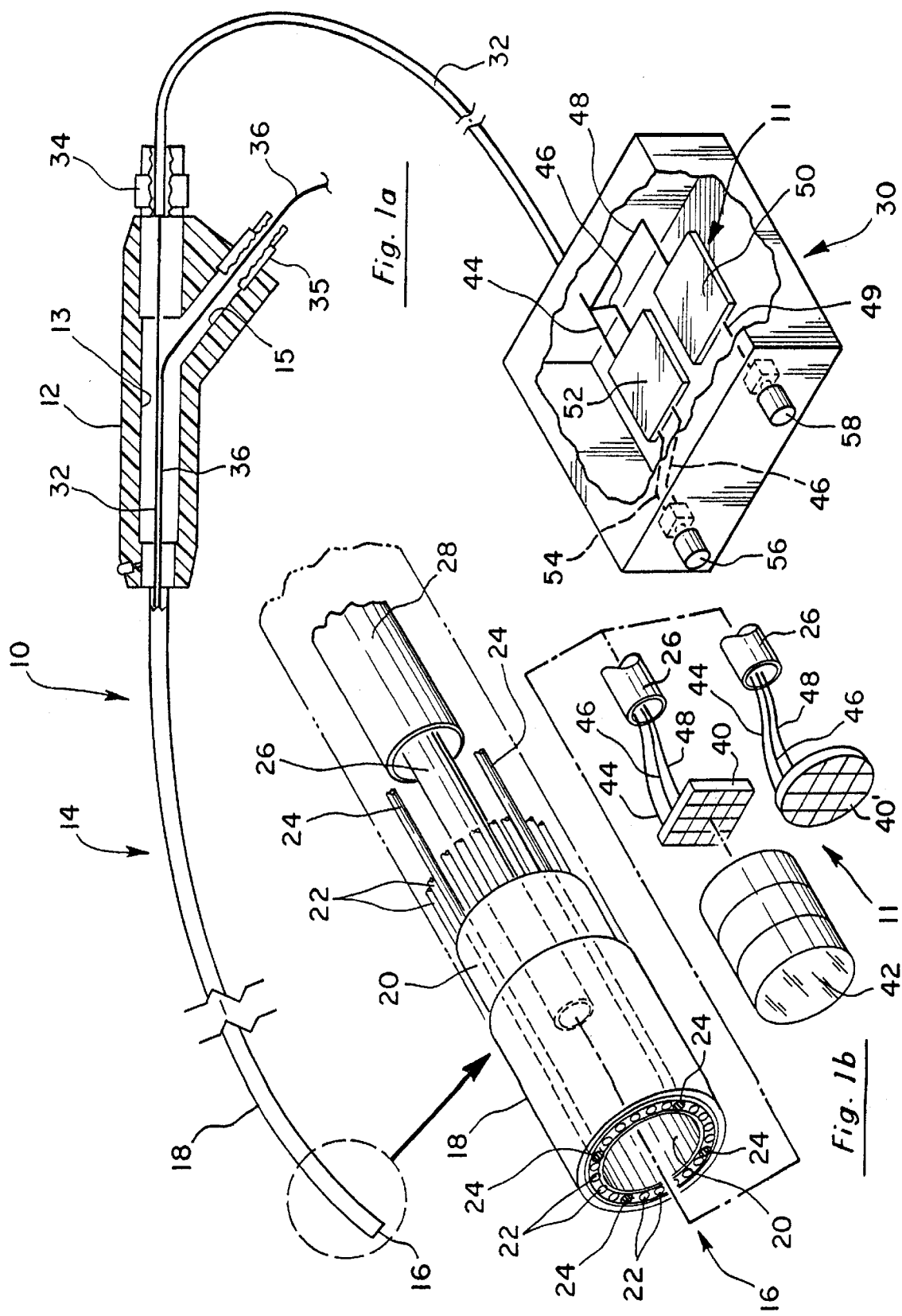

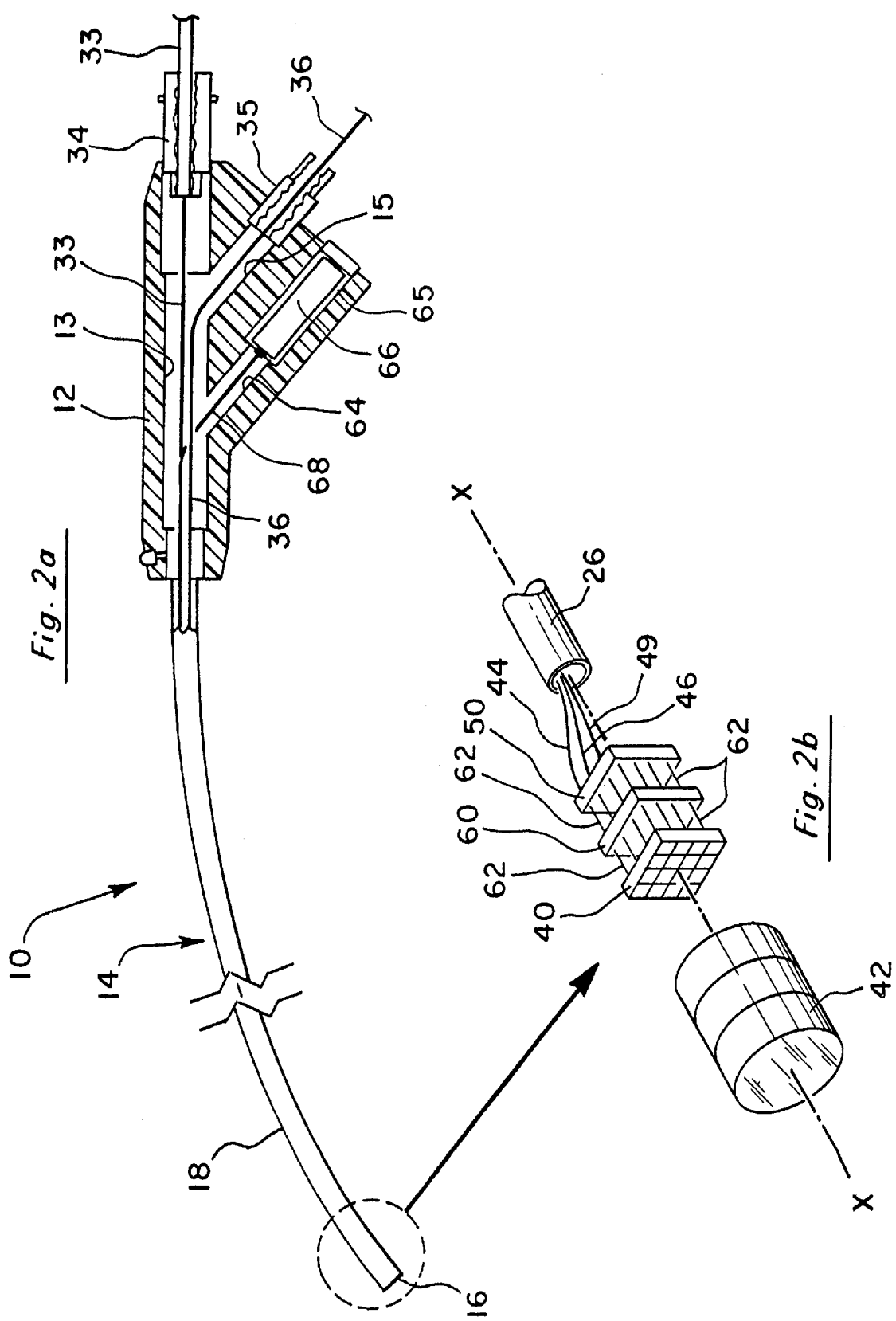

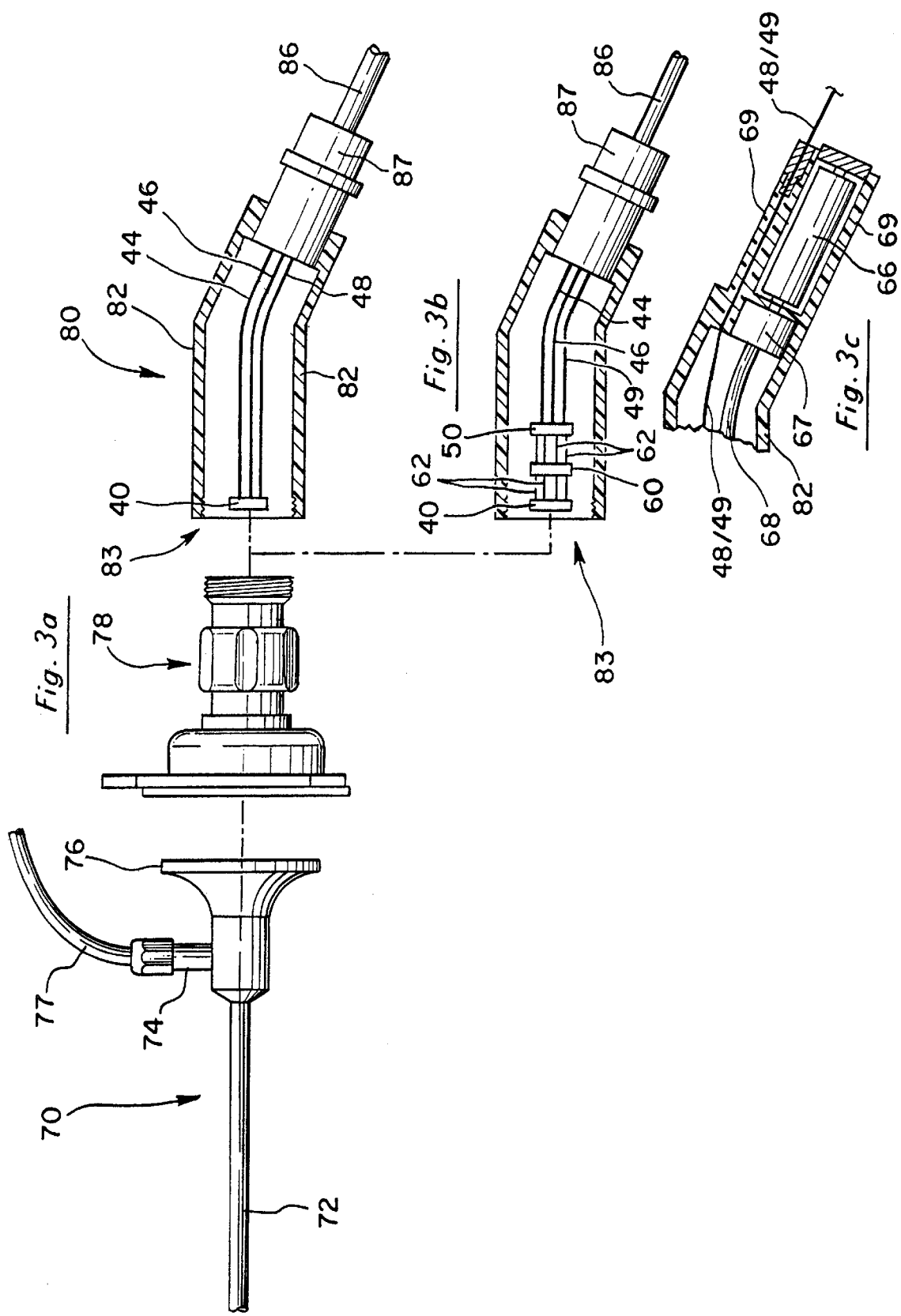

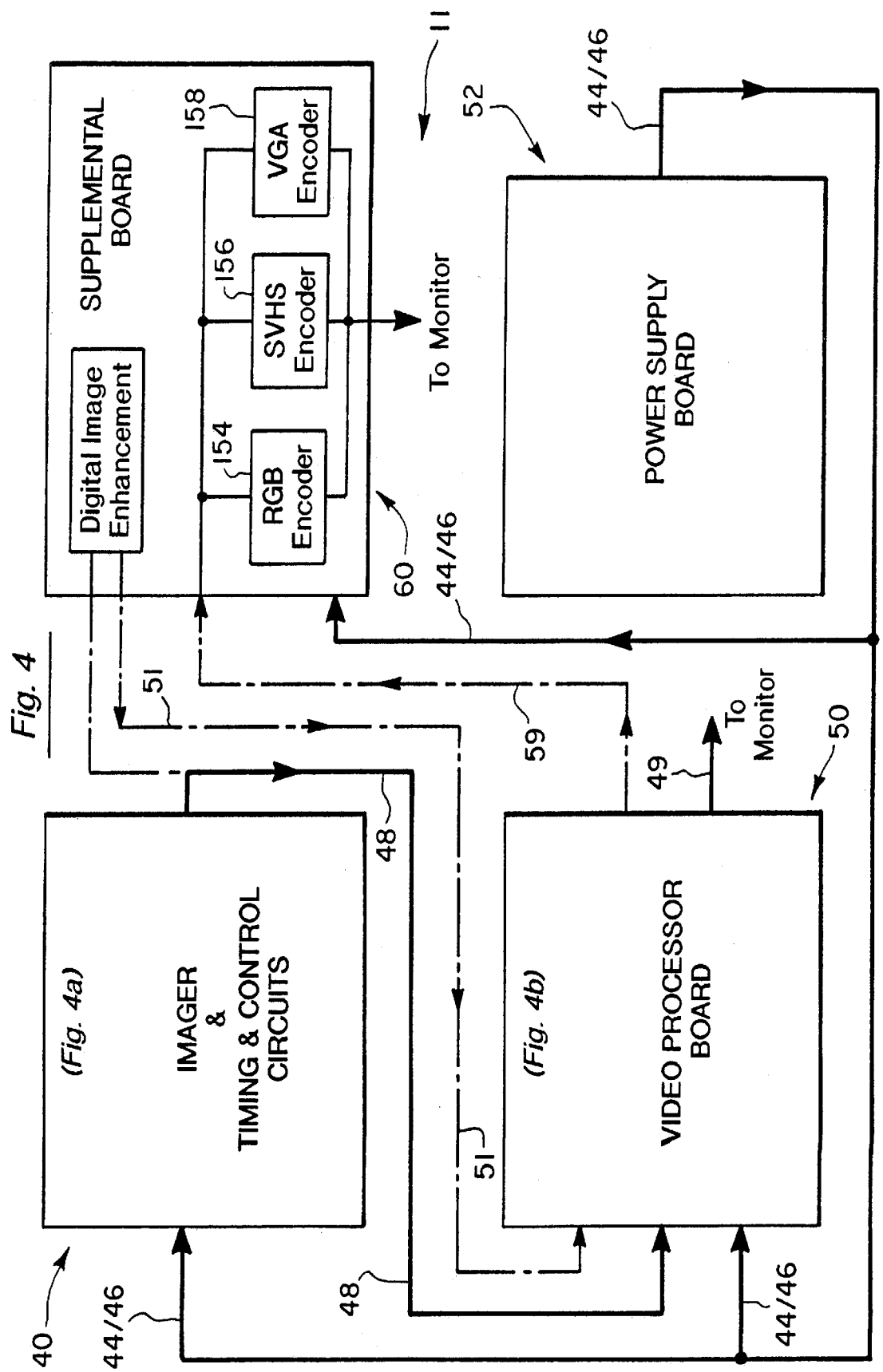

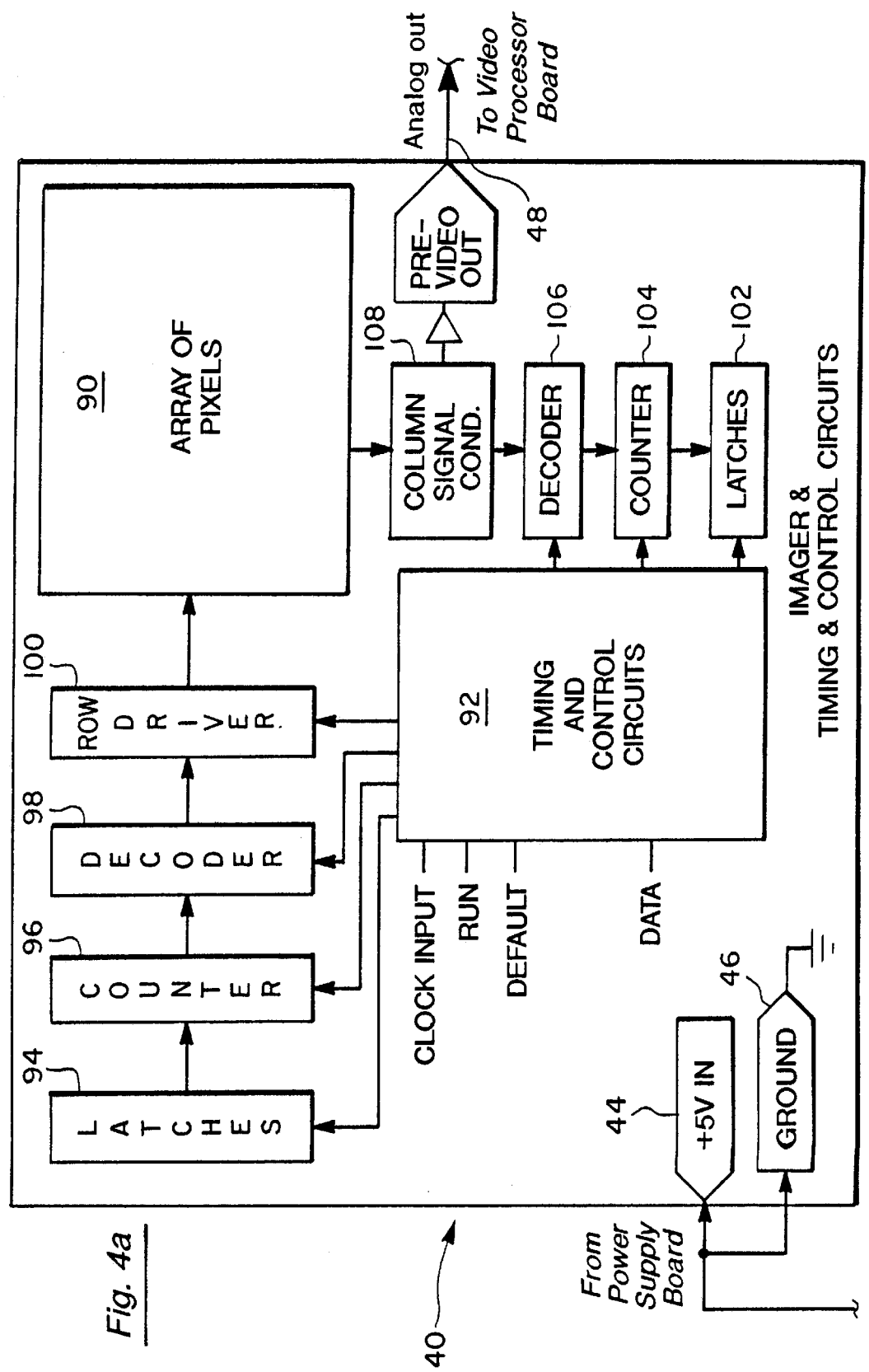

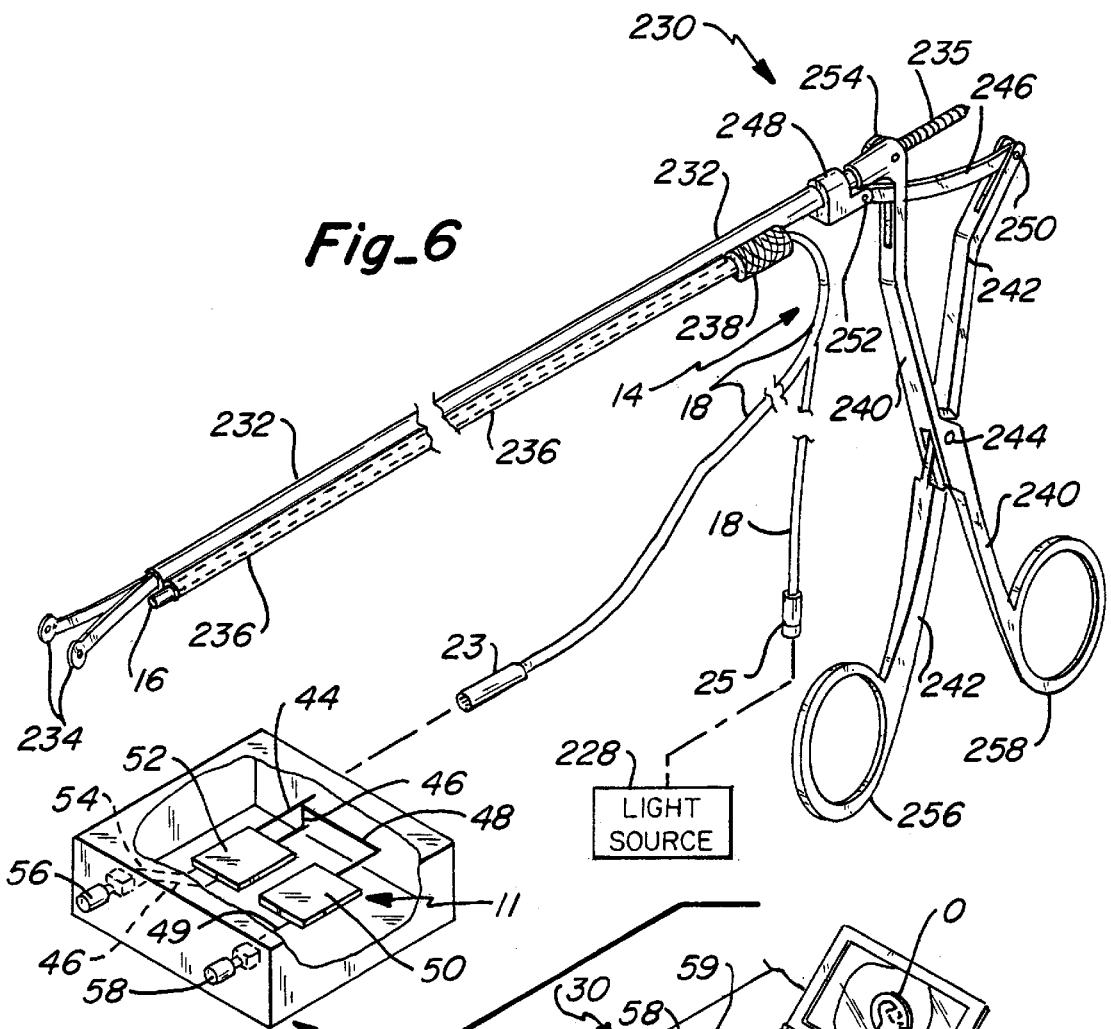
Fig_6
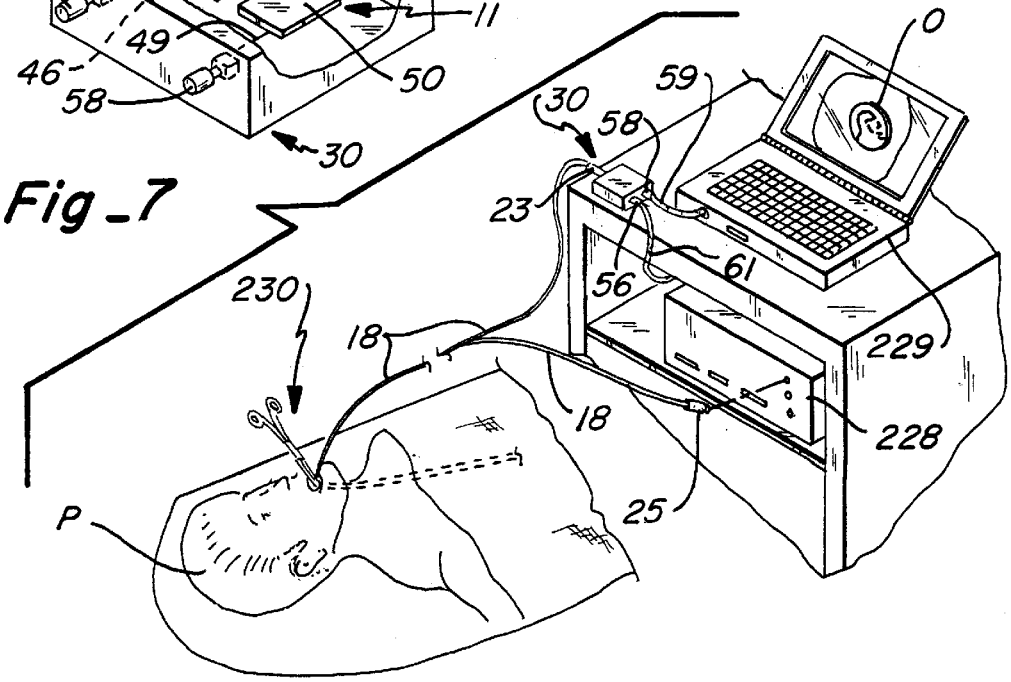
Fig_7

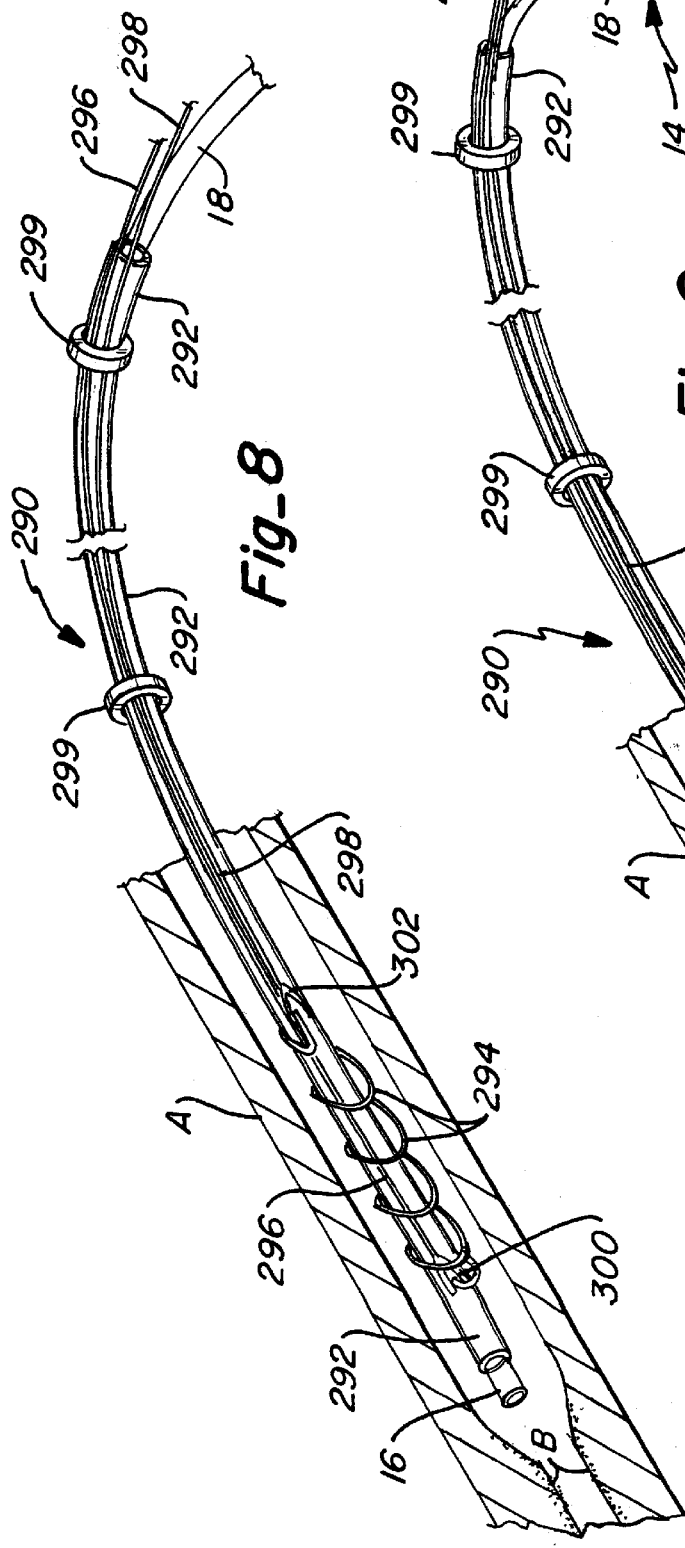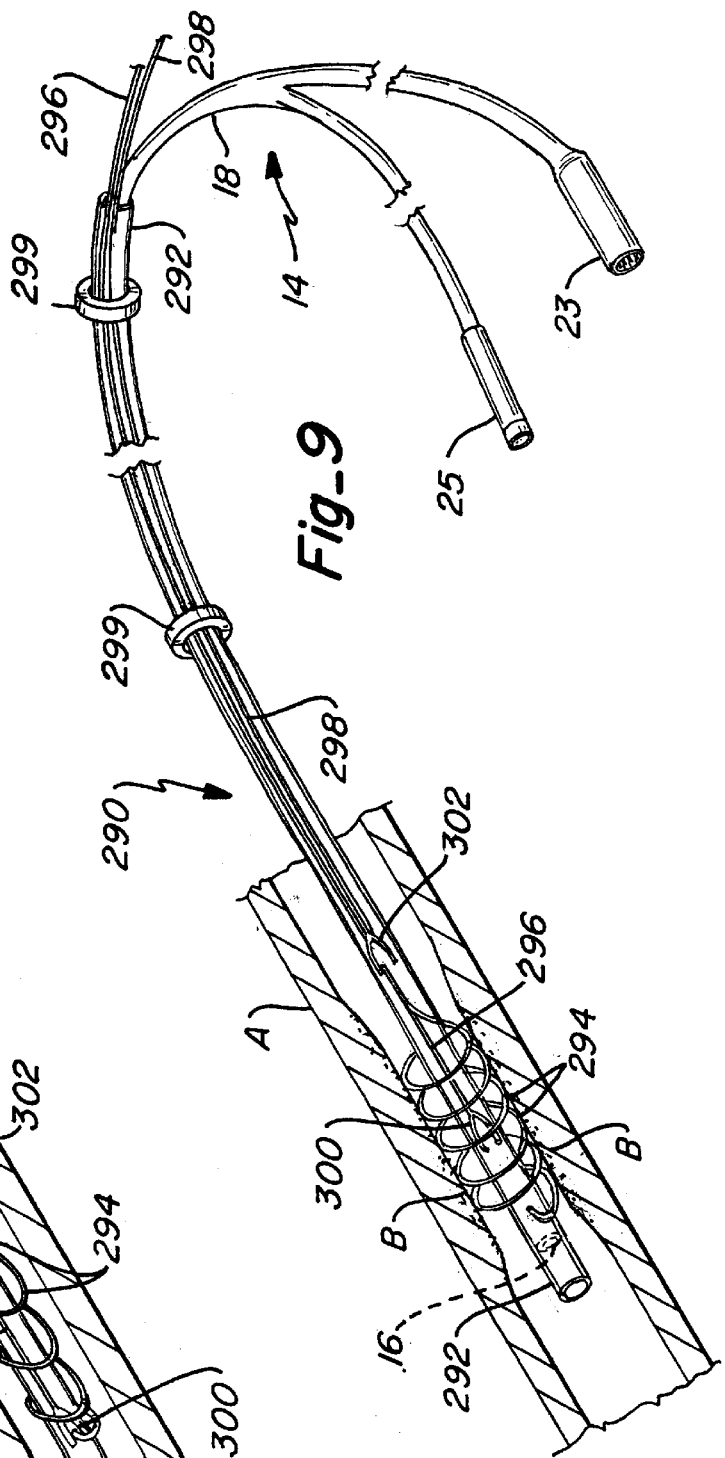

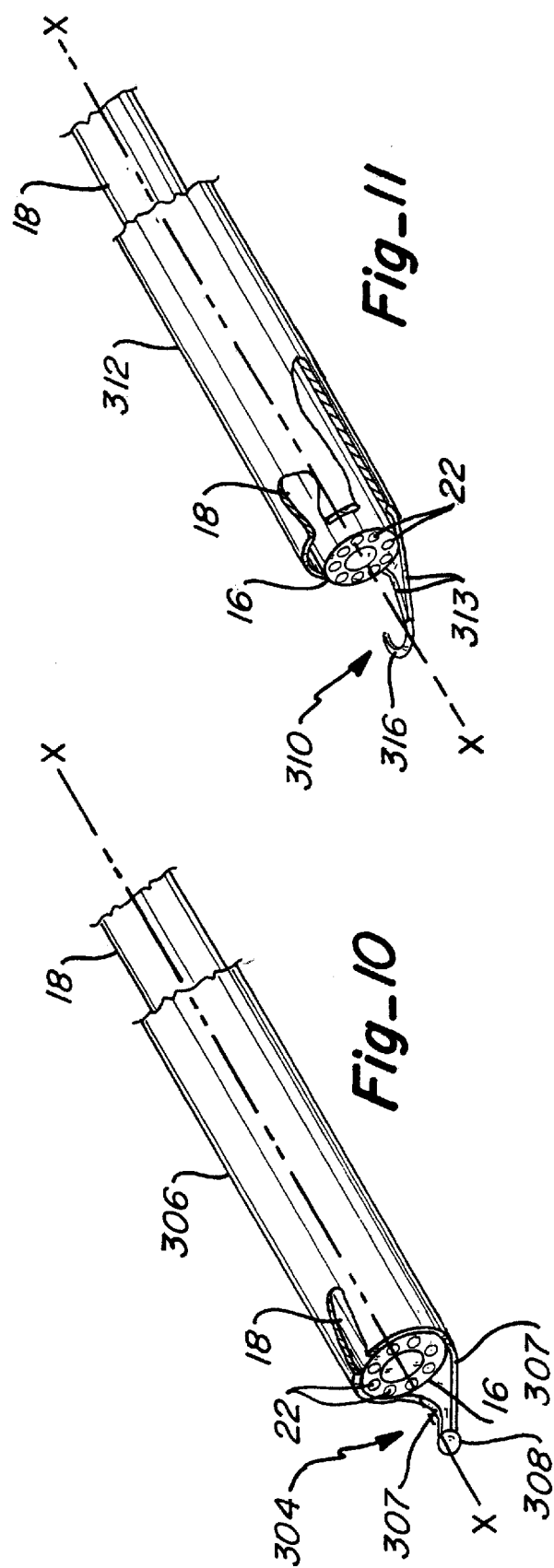

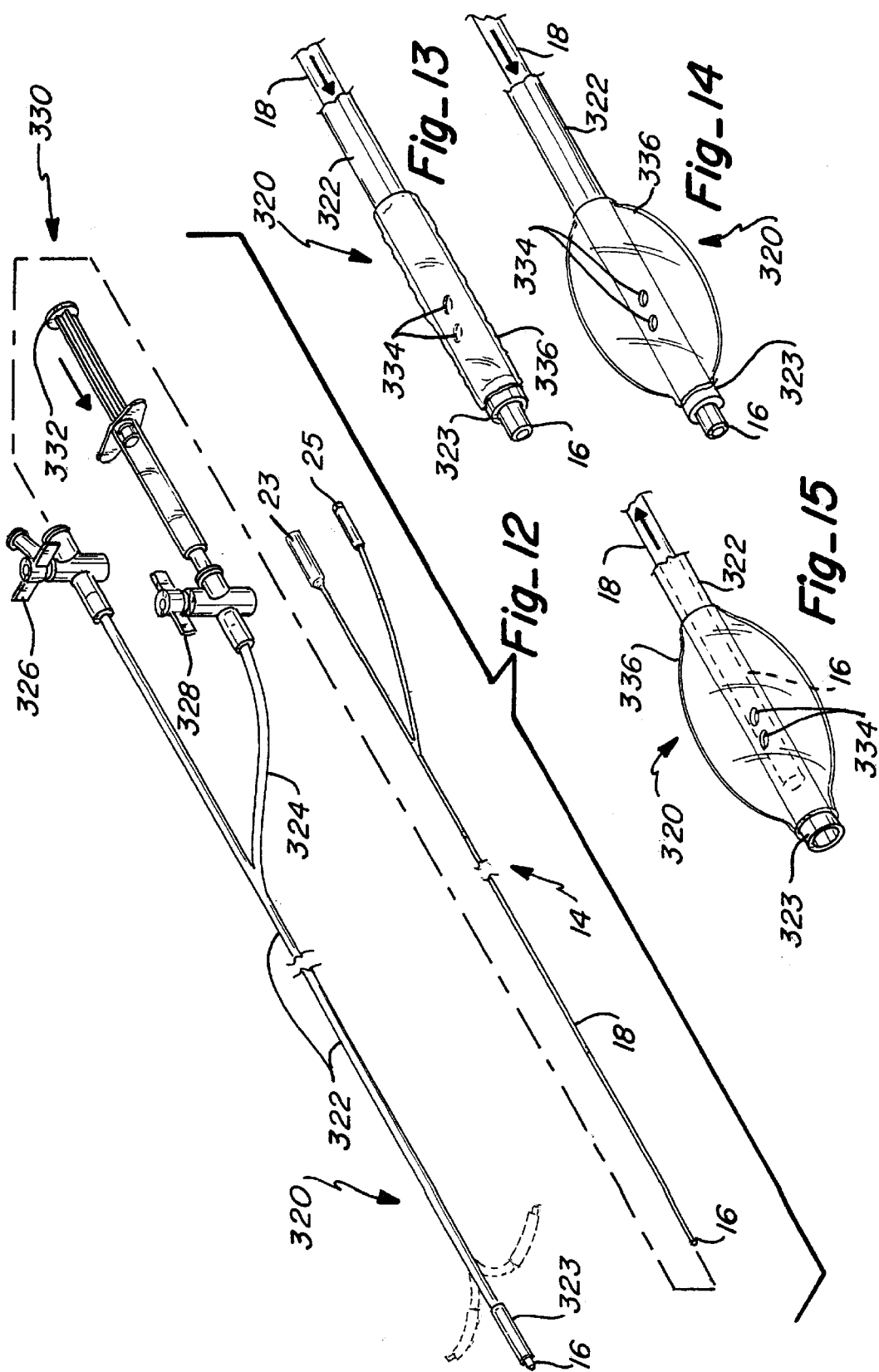

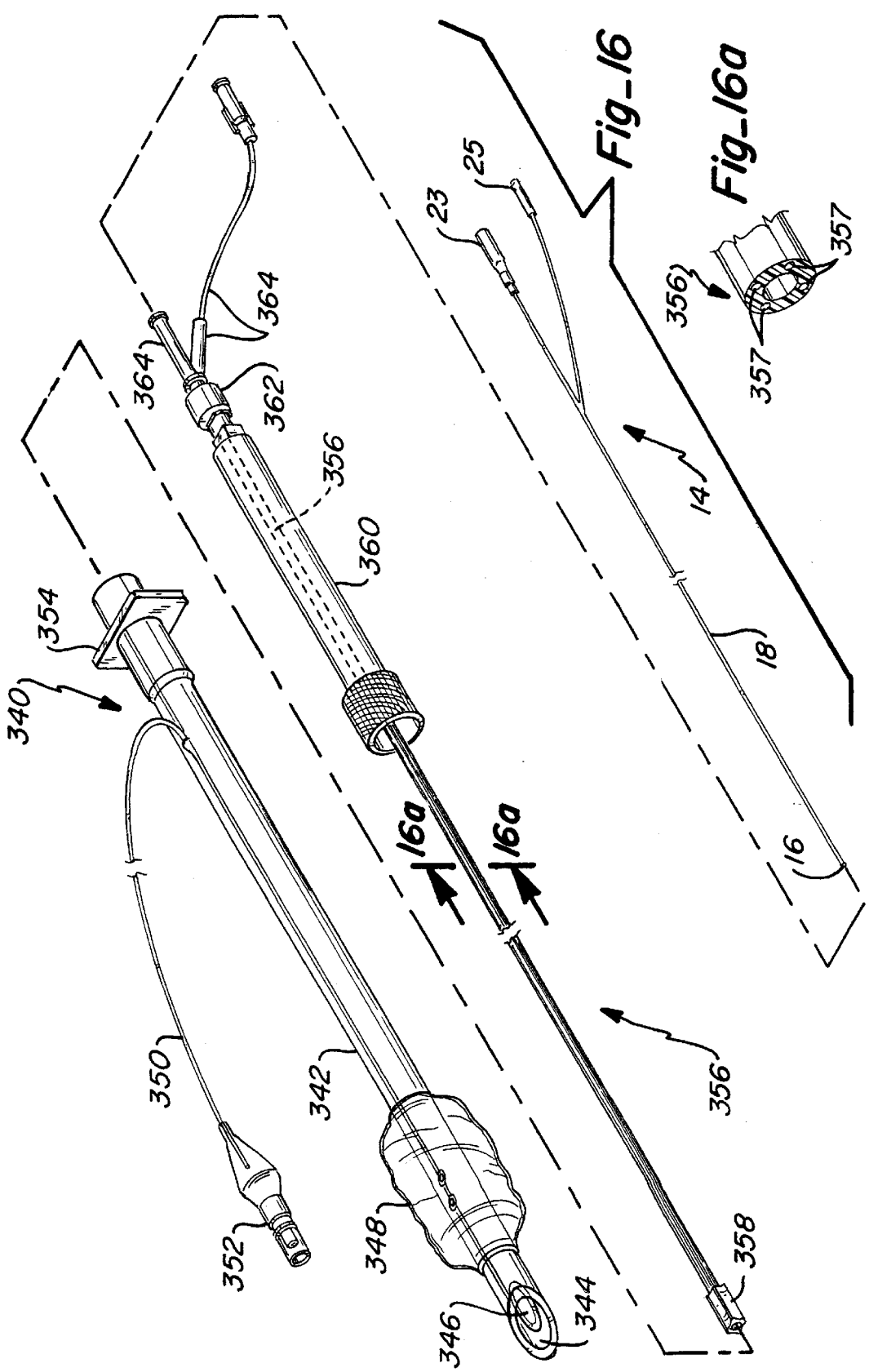

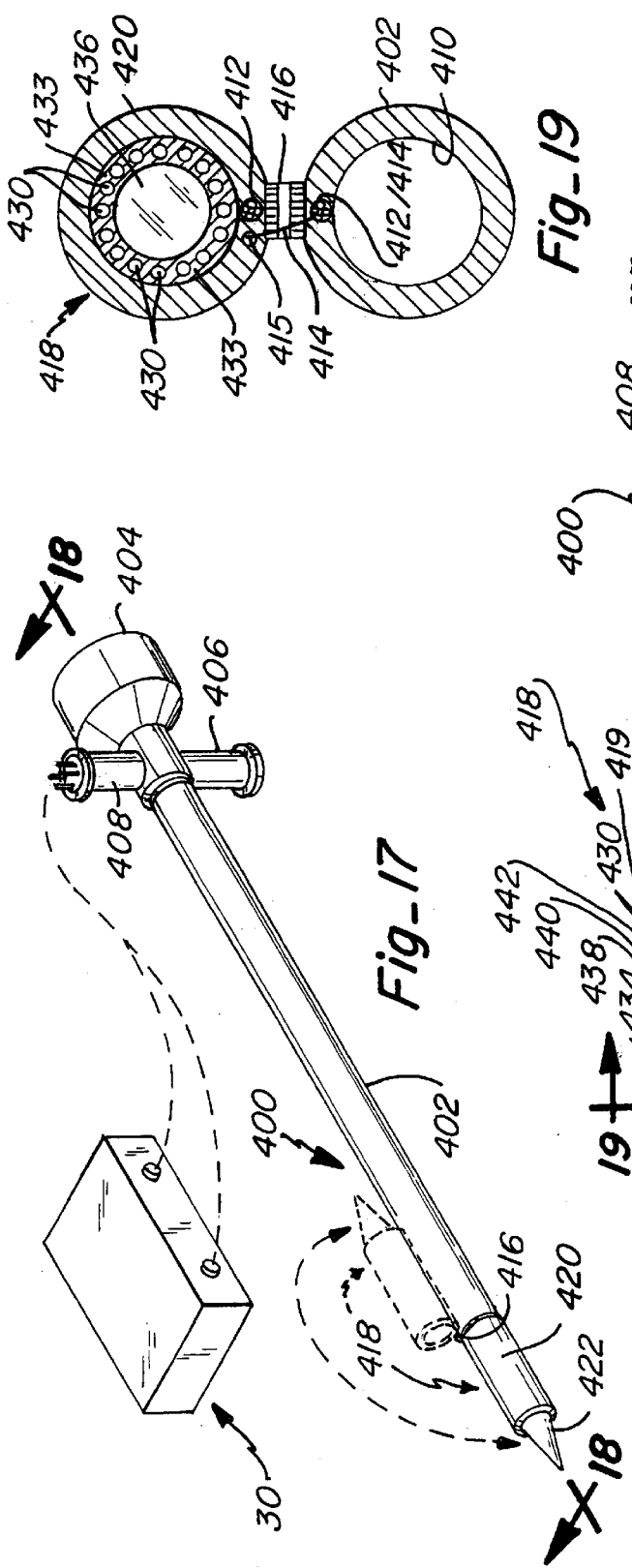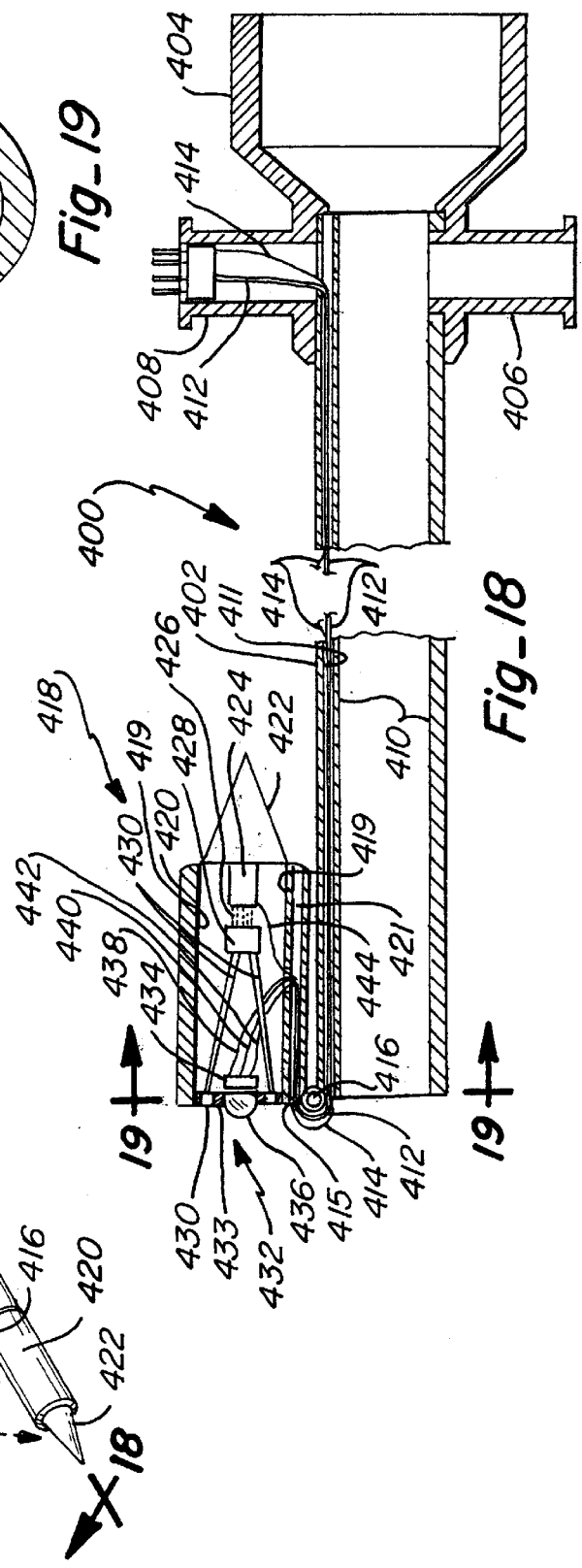

SURGICAL DEVICES INCORPORATING REDUCED AREA IMAGING DEVICES

This application is a continuation-in-part of U.S. Ser. No. 09/496,312, filed on Feb. 1, 2000, entitled "Reduced Area Imaging Devices," which is a continuation of U.S. Ser. No. 09/175,685, filed Oct. 20, 1998, now U.S. Pat. No. 6,043, 839 entitled "Reduced Area Imaging Devices," which is a continuation-in-part of U.S. Ser. No. 08/944,322, filed Oct. 6, 1997, now U.S. Pat. No. 5,929,901 entitled "Reduced Area Imaging Devices Incorporated Within Surgical Instruments," and this application is also a continuation-in-part of U.S. Ser. No. 08/927,785, filed on Sep. 11, 1997, now U.S. Pat. No. 6,086,528 entitled "Surgical Devices With Removable Imaging Capability and Methods of Employing Same."

TECHNICAL FIELD

This invention relates to solid state image sensors and associated electronics incorporated within surgical devices, and more particularly, to solid state image sensors which are configured to be of a minimum size and which are used in combination with surgical devices allowing certain medical procedures to be conducted in more efficient, less invasive, and safer ways.

BACKGROUND ART

In recent years, endoscopic surgery has become the accepted standard for conducting many types of surgical procedures, both in the medical and dental arenas. The availability of imaging devices enabling a surgeon or dentist to view a particular surgical area through a small diameter endoscope which is introduced into small cavities or openings in the body results in much less patient trauma as well as many other advantages.

In many hospitals, the rod lens endoscope is still used in endoscopic surgery. The rod lens endoscope includes a very precise group of lenses in an elongate and rigid tube which are able to accurately transmit an image to a remote camera in line with the lens group. The rod lens endoscope, because of its cost of manufacture, failure rate, and requirement to be housed within a rigid and straight housing, is being increasingly replaced by solid state imaging technology which enables the image sensor to be placed at the distal tip of the investigating device. The three most common solid state image sensors include charged coupled devices (CCD), charge injection devices (CID) and photo diode arrays (PDA). In the mid-1980s complementary metal oxide semiconductors (CMOS) were developed for industrial use. CMOS imaging devices offer improved functionality and simplified system interfacing. Furthermore, many CMOS imagers can be manufactured at a fraction of the cost of other solid state imaging technologies.

One particular advance in CMOS technology has been in the active pixel-type CMOS imagers which consist of randomly accessible pixels with an amplifier at each pixel site. One advantage of active pixel-type imagers is that the amplifier placement results in lower noise levels than CCDs or other solid state imagers. Another major advantage is that these CMOS imagers can be mass produced on standard semiconductor production lines. One particularly notable advance in the area of CMOS imagers including active pixel-type arrays is the CMOS imager described in U.S. Pat. No. 5,471,515 to Fossum, et al. This CMOS imager can incorporate a number of other different electronic controls that are usually found on multiple circuit boards of much larger size. For example, timing circuits, and special functions such as zoom and anti-jitter controls can be placed on the same circuit board containing the CMOS pixel array without significantly increasing the overall size of the host circuit board. Furthermore, this particular CMOS imager requires 100 times less power than a CCD-type imager. In short, the CMOS imager disclosed in Fossum, et al. has enabled the development of a "camera on a chip."

Passive pixel-type CMOS imagers have also been improved so that they too can be used in an imaging device which qualifies as a "camera on a chip." In short, the major difference between passive and active CMOS pixel arrays is that a passive pixel-type imager does not perform signal amplification at each pixel site. One example of a manufacturer which has developed a passive pixel array with performance nearly equal to known active pixel devices and being compatible with the read out circuitry disclosed in the U.S. Pat. No. 5,471,515 is VLSI Vision, Ltd., 1190 Saratoga Avenue, Suite 180, San Jose, Calif. 95129. A further description of this passive pixel device may be found in co-pending application, Ser. No. 08/976,976, entitled "Reduced Area Imaging Devices Incorporated Within Surgical Instruments," and is hereby incorporated by reference.

In addition to the active pixel-type CMOS imager which is disclosed in U.S. Pat. No. 5,471,515, there have been developments in the industry for other solid state imagers which have resulted in the ability to have a "camera on a chip." For example, Suni Microsystems, Inc. of Mountain View, Calif., has developed a CCD/CMOS hybrid which combines the high quality image processing of CCDs with standard CMOS circuitry construction. In short, Suni Microsystems, Inc. has modified the standard CMOS and CCD manufacturing processes to create a hybrid process providing CCD components with their own substrate which is separate from the P well and N well substrates used by the CMOS components. Accordingly, the CCD and CMOS components of the hybrid may reside on different regions of the same chip or wafer. Additionally, this hybrid is able to run on a low power source (5 volts) which is normally not possible on standard CCD imagers which require 10 to 30 volt power supplies. A brief explanation of this CCD/CMOS hybrid can be found in the article entitled "Startup Suni Bets on Integrated Process" found in *Electronic News*, Jan. 20, 1997 issue. This reference is hereby incorporated by reference for purposes of explaining this particular type of imaging processor.

Another example of a recent development in solid state imaging is the development of a CMOS image sensor which is able to achieve analog to digital conversion on each of the pixels within the pixel array. This type of improved CMOS imager includes transistors at every pixel to provide digital instead of analog output that enable the delivery of decoders and sense amplifiers much like standard memory chips. With this new technology, it may, therefore, be possible to manufacture a true digital "camera on a chip." This CMOS imager has been developed by a Stanford University joint project and is headed by Professor Abbas el-Gamal.

A second approach to creating a CMOS-based digital imaging device includes the use of an over-sample converter at each pixel with a one bit comparator placed at the edge of the pixel array instead of performing all of the analog to digital functions on the pixel. This new design technology has been called MOSAD (multiplexed over sample analog to digital) conversion. The result of this new process is low power usage, along with the capability to achieve enhanced dynamic range, possibly up to 20 bits. This process has been developed by Amain Electronics of Simi Valley, Calif. A brief description of both of the processes developed by Stanford University and Amain Electronics can be found in an article entitled "A/D Conversion Revolution for CMOS Sensor?," September 1998 issue of *Advanced Imaging*. This reference is also hereby incorporated by reference for purposes of explaining these particular types of imaging processors.

Yet another example of a recent development with respect to sol id state imaging is an imaging device developed by Shell Case, of Jerusalem, Israel. In an article entitled "A CSP Optoelectronic Package for Imaging and Light Detection Applications" (A. Badihi), Shell Case introduces a die-sized, ultrathin optoelectronic package which is completely packaged at the wafer level using semiconductor processing. In short, Shell Case provides a chip scale package (CSP) process for accepting digital image sensors which may be used, for example, in miniature cameras. The die-sized, ultrathin package is produced through a wafer level process which utilizes optically clear materials and completely encases the imager die. This packaging method, ideally suited for optoelectronic devices, results in superior optical performance and form factor not available by traditional image sensors. This reference is also incorporated by reference for purposes of explaining Shell Case's chip scale package process.

Yet another example of a recent development with respect to solid state imaging is shown in U.S. Pat. No. 6,020,581 entitled "Solid State CMOS Imager Using Silicon On Insulator or Bulk Silicon." This patent discloses an image sensor incorporating a plurality of detector cells arranged in an array wherein each detector cell has a MOSFET with a floating body and operable as a lateral bipolar transistor to amplify charge collected by the floating body. This reference overcomes problems of insufficient charge being collected in detector cells formed on silicon on insulator (SOI) substrates due to silicon thickness and will also work in bulk silicon embodiments.

The above-mentioned developments in solid state imaging technology have shown that "camera on a chip" devices will continue to be enhanced not only in terms of the quality of imaging which may be achieved, but also in the specific construction of the devices which may be manufactured by new breakthrough processes.

Although the "camera on a chip" concept is one which has great merit for application in many industrial areas, a need still exists for a reduced area imaging device which can be used in even the smallest type of endoscopic instruments in order to view areas in the body that are particularly difficult to access, and to further minimize patient trauma by an even smaller diameter invasive instrument.

It is one object of this invention to provide reduced area imaging devices which take advantage of "camera on a chip" technology, but rearrange the circuitry in a stacked relationship so that there is a minimum profile presented when used within a surgical instrument or other investigative device. It is another object of this invention to provide low cost imaging devices which may be "disposable." It is yet another object of this invention to provide reduced area imaging devices which may be used in conjunction with standard endoscopes by placing the imaging device through channels which normally receive other surgical devices, or receive liquids or gases for flushing a surgical area. It is yet another object of this invention to provide a surgical device with imaging capability which may be battery powered and only requires one conductor for transmitting a pre-video signal to video processing circuitry within or outside the sterile field of the surgical area.

In addition to the intended use of the foregoing invention with respect to surgical procedures conducted by medical doctors, it is also contemplated that the invention described herein has great utility with respect to oral surgery and general dental procedures wherein a very small imaging device can be used to provide an image of particularly difficult to access locations. Additionally, while the foregoing invention has application with respect to the medical and dental fields, it will also be appreciated by those skilled in the art that the small size of the imaging device set forth herein can be applied to other functional disciplines wherein the imaging device can be used to view difficult to access locations for industrial equipment and the like. Therefore, the imaging device of this invention could be used to replace many industrial boroscopes.

The "camera on a chip" technology can be furthered improved with respect to reducing its profile area and incorporating such a reduced area imaging device into very small investigative instruments which can be used in the medical, dental, or other industrial fields.

Because of the sophisticated optics and circuitry contained in modern endoscopes, they can be very expensive and difficult to maintain. Additionally, since the size of the endoscope is still a major concern in endoscopic procedures, standard surgical instruments must be modified to reduce their size in order that the instruments can be used simultaneously with the endoscope. For example, it is well-known in the art to provide a plurality of channels within or around the endoscope in order that miniature surgical instruments such as forceps or the like may be simultaneously introduced with the endoscope. Therefore, the construction of most prior art endoscopes begins first with consideration of the size of the endoscope, and then operative channels are formed within or around the endoscope so that the modified surgical instrument may be introduced simultaneously to the site under investigation.

Although great advances have been made in the electronic industry in terms of reducing the size of the imaging elements which are used within the endoscope, many endoscopes in use continue to be too large to conduct certain surgical procedures. Additionally, many surgical procedures cannot be effectively conducted with the miniaturized surgical instruments. Rather, a more full size surgical instrument is still required. Furthermore, cost continues to be a prohibitive factor because the special surgical instruments must be manufactured which are small enough to fit within the small channels of the endoscope being used.

From the foregoing, it is apparent that an even smaller imaging device is desirable which can be used universally with larger and more standard sized surgical instruments in order to reduce the cost of providing endoscopic capability for certain surgical procedures as well as maintaining a minimally invasive sized instrument with imaging capability which is used to conduct such surgical procedures. Accordingly, the imaging device of this invention is ideally suited to overcome the shortcomings of most modern endoscopes discussed above.

DISCLOSURE OF THE INVENTION

In accordance with the present invention, reduced area imaging devices are provided in combination with modified surgical instruments. The term "imaging device" as used herein describes the imaging elements and processing circuitry which is used to produce a video signal which may be accepted by a standard video device such as a television or video monitor accompanying a personal computer. The term "image sensor" as used herein describes the components of a solid state imaging device which captures images and stores them within the structure of each of the pixels in the array of pixels found in the imaging device. As further discussed below, the timing and control circuits can be placed either on the same planar structure as the pixel array, in which case the image sensor can also be defined as an integrated circuit, or the timing and control circuitry can be placed remote from the pixel array. The terms "signal" or "image signal" as used herein, and unless otherwise more specifically defined, refer to an image which at some point during its processing by the imaging device, is found in the form of electrons which have been placed in a specific format or domain. The term "processing circuitry" as used herein refers to the electronic components within the imaging device which receive the image signal from the image sensor and ultimately place the image signal in a usable format. The terms "timing and control circuits" or "circuitry" as used herein refer to the electronic components which control the release of the image signal from the pixel array.

In a first configuration, the image sensor, with or without the timing and control circuitry, may be placed at the distal tip of the endoscopic instrument while the remaining processing circuitry may be found in a small remote control box which may communicate with the image sensor by a single cable.

In a second configuration, the image sensor and the processing circuitry may all be placed in a stacked arrangement of circuit boards and positioned at the distal tip of the endoscopic instrument. In this embodiment, the pixel array of the image sensor may be placed by itself on its own circuit board while the timing and control circuitry and processing circuitry are placed on one or more other circuit boards. Alternatively, the circuitry for timing and control may be placed with the pixel array on one circuit board, while the remaining processing circuitry can be placed on one or more of the other circuit boards.

For the configuration of the imaging device which calls for the array of pixels and the timing and control circuitry to be placed on the same circuit board, only one conductor is required in order to transmit the image signal to the processing circuitry. In the other configuration of the imaging device wherein the timing and control circuits are incorporated onto other circuit boards, a plurality of connections are required in order to connect the timing and control circuitry to the pixel array and the one conductor is also required to transmit the image signal.

In yet another configuration, the imaging device may be adapted for use with a standard rod lens endoscope wherein the imaging device is placed within a standard camera housing which is configured to connect to a standard "C" or "V" mount connector.

Also in accordance with this invention, the reduced area imaging devices are not restricted to any special or particular type of silicon wafer manufacturing technology, and can be incorporated within not only known integrated circuit manufacturing processes, but also those which are now emerging. For example, silicon on insulator (SOI) is a new emerging technology increasingly recognized by innovative circuit manufacturers for its ability to bring enhanced performance and reduced power consumption due to dense microprocessors and telecommunication integrated circuits. In short, SOI is wafer technology which includes the addition of an insulating layer formed over the standard silicon wafer, and then adding an additional silicon wafer over the top of the insulating layer. SOI prevents substrate leakage that is prevalent in conventional integrated circuits, and allows increased clock speeds and much lower supply voltages. Recently, SOI has been optimized for the basic pixel structures found in video cameras. It should be noted that SOI technology is mechanical in nature and does not affect basic circuit architecture whether it be CMOS or other types of architecture. In the present invention, the bulk of the CMOS circuitry could simply be implanted in the uppermost silicon layer of an SOI integrated circuit.

A very small endoscope may be created using the imaging device of the first or second configurations. This very small endoscope may be referred to as a "microendoscope" which simply includes a very small diameter tubular portion or sheath which is inserted within the patient. The tubular portion or sheath may be made of a flexible material having a central lumen or opening therein for receiving the elements of the preferred imaging device. The tubular portion may be modified to include an additional concentric tube placed within the central lumen and which enables a plurality of light fibers to be placed circumferentially around the periphery of the distal end of the tubular portion. Additionally, control wires may extend along the tubular portion in order to make the endoscope steerable. The proximal end of the tubular portion can simply include the connections necessary to allow the image signal to be further processed or to be connected directly to a video control device, and to allow a desired light source to provide light to the light fibers. In a more conventional type of endoscope, a handle can be included which allows the user to better grasp and hold the device. The material used to make the microendoscope/endoscope can be compatible with any desired sterilization protocol, or the entire microendoscope/endoscope can be made sterile and disposable after use.

In one application, the microendoscope of this invention may be used in conjunction with standard Jackson grasping forceps which have been modified to include a longitudinal tube or channel for which to receive the microendoscope. In use, the microendoscope provides an integral imaging capability while the surgeon manipulates the Jackson grasping forceps for removal of a foreign object within a patient.

In another application, the microendoscope may be used in conjunction with a stent placement catheter. In this application, the microendoscope is placed through the small diameter tube of the catheter to provide integral imaging capability for guiding the catheter to the precise location in the body at which the stent is to be positioned.

In another application, the microendoscope of this invention may be used in conjunction with an "over-tube" dissecting or tissue separating device in order to conduct very precise cutting, tissue separating or fulgeration procedures.

In another application, the microendoscope may be used in conjunction with a steerable balloon catheter in much the same manner as the microendoscope is used with the stent placement catheter.

In yet another application, the microendoscope may be used with an endotracheal intubation device allowing a user to view the placement of the endotracheal tube within a patient.

In yet another application, the reduced area imaging devices of this invention can be incorporated directly into a modified entry trochar or may be used in conjunction with the microendoscope.

In all of the applications, the microendoscope may be provided with light from a light source which causes the light fibers to illuminate the surgical area according to a desired type of light. For example, the microendoscope of this invention is ideally suited for fluorescence detection endoscopy and other procedures which require special frequencies of light, e.g., 200–1100 Nm.

These and other advantages will become apparent to those skilled in the art in view of the description of the drawings and the description of the preferred embodiments which follow.

BRIEF DESCRIPTION OF THE DRAWINGS

FIG. 1a illustrates an endoscope in a fragmentary cross-sectional view, and a fragmentary perspective view of a control box, the endoscope and control box each incorporating elements of a reduced area imaging device;

FIG. 1b is an enlarged fragmentary partially exploded perspective view of the distal end of the endoscopic instrument specifically illustrating the arrangement of the image sensor with respect to the other elements of the tubular portion of the endoscope;

FIG. 2a is a fragmentary cross-sectional view of another configuration of the imaging device of this invention used within an endoscope wherein the imaging device is incorporated in its entirety at the distal tip of the endoscope;

FIG. 2b is an enlarged fragmentary partially exploded perspective view of the distal end of the endoscope of FIG. 2a illustrating the imaging device;

FIG. 3a is an elevational fragmentary cross-sectional view of the image sensor incorporated with a standard camera housing for connection to a rod lens endoscope;

FIG. 3b is a fragmentary cross-sectional view of the imaging device incorporated within the camera housing of FIG. 3a;

FIG. 3c is a fragmentary cross-sectional view similar to that of FIG. 3b illustrating a battery as an alternate source of power;

FIG. 4 is a schematic diagram of the functional electronic components which make up the imaging device;

FIG. 4a is an enlarged schematic diagram of a circuit board which may include the array of pixels and the timing and control circuitry;

FIG. 6 is a perspective view of the microendoscope used in conjunction with Jackson grasping forceps;

FIG. 7 is a perspective view of a patient undergoing a surgical procedure to remove a foreign object such as a coin from the patient's lungs or trachea by use of the Jackson grasping forceps with imaging capability.

FIG. 8 is an enlarged fragmentary perspective view of the microendoscope used in conjunction with a stent placement catheter;

FIG. 9 is another fragmentary perspective view of the microendoscope used in conjunction with the stent placement catheter wherein the stent placement catheter has been positioned within a desired location within the patient's body and the stent has been activated to allow removal of the catheter and microendoscope;

FIG. 10 is a greatly enlarged fragmentary perspective view of the microendoscope used in conjunction with an over-tube tissue separating device;

FIG. 11 is a fragmentary perspective view of the microendoscope used in con junction with an over tube dissecting device used for cutting tissue or ligation;

FIG. 12 is a perspective, exploded view of a balloon catheter and the microendoscope prior to its insertion within the catheter;

FIG. 13 is a fragmentary perspective view of the balloon catheter with the microendoscope inserted therethrough prior to inflation of the balloon portion;

FIG. 14 is another fragmentary perspective view of the microendoscope inserted through the balloon catheter after the balloon portion has inflated;

FIG. 15 is yet another fragmentary perspective view as in FIGS. 13 and 14 illustrating the microendoscope being removed from within the balloon catheter;

FIG. 16 is an exploded perspective view of an endotracheal intubation device and the microendoscope prior to its insertion within the endotracheal tube;

FIG. 16a is an enlarged fragmentary perspective view of the centering tube used with the endotracheal intubation device, taken along line 16—16 of FIG. 16;

FIG. 17 is a perspective view of an entry trochar which may incorporate the reduced area imaging device of this invention;

FIG. 18 is an enlarged vertical section taken along line 18—18 of FIG. 17 illustrating the interior details of the embodiments; and FIG. 19 is a greatly enlarged vertical section taken along line 19—19 of FIG. 18.

BEST MODE FOR CARRYING OUT THE INVENTION

Figure 4B:
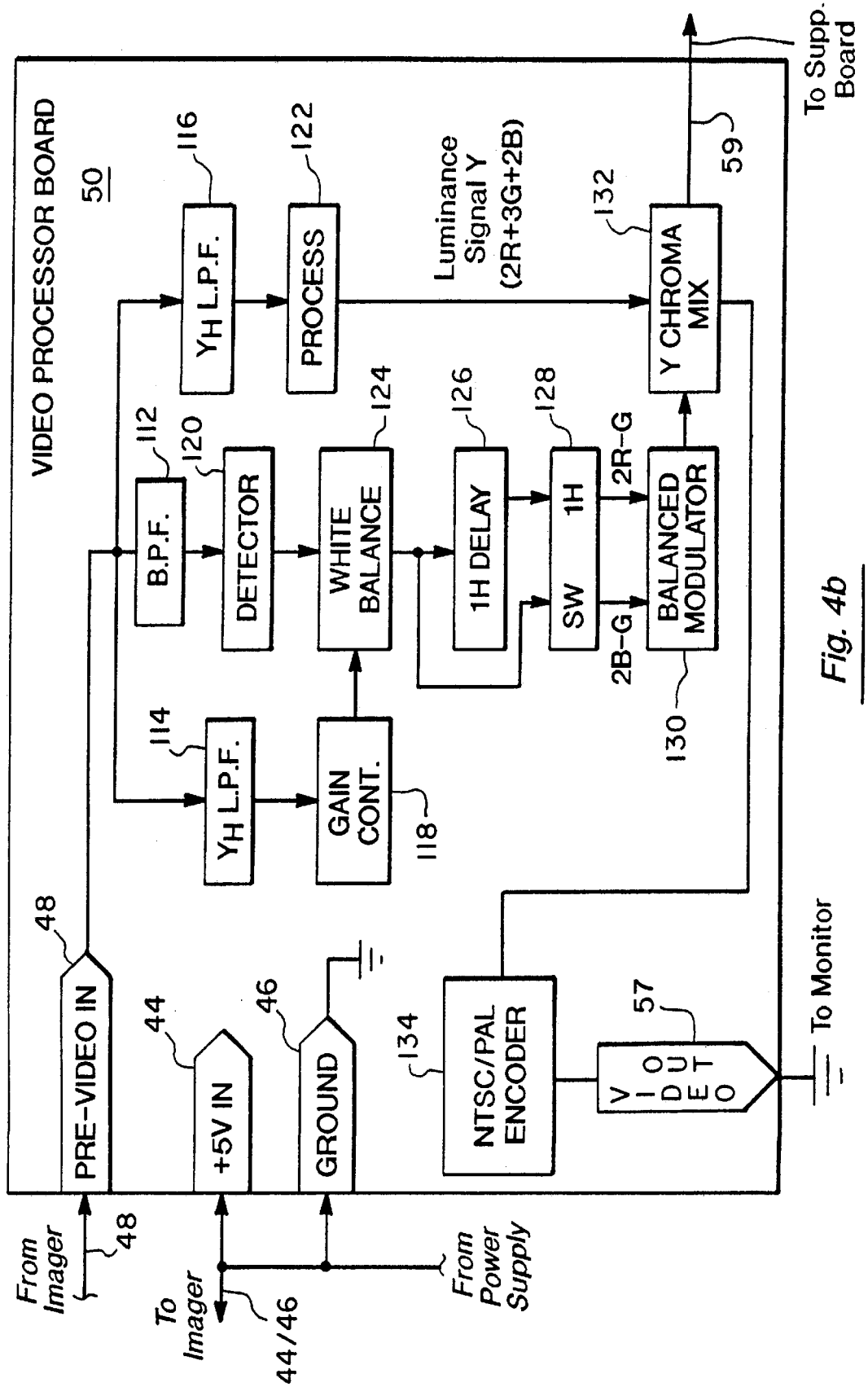
FIG. 4b is an enlarged schematic diagram of a video processing board having placed thereon the processing circuitry which processes the pre-video signal generated by the array of pixels and which converts the pre-video signal to a post-video signal which may be accepted by a standard video device.

In accordance with the invention as shown in FIG. 1a, an endoscope 10 is provided which incorporates a reduced area imaging device 11, shown in FIG. 1b. As further discussed below, the elements of the imaging device may all be found at one location or the elements may be separated from one another and interconnected by the appropriate cable(s). The array of pixels making up the image sensor captures images and stores them in the form of electrical energy by conversion of light photons to electrons. This conversion takes place by the photo diodes in each pixel which communicate with one or more capacitors which store the electrons. The structure of the endoscope 10 includes a flexible or rigid tubular portion 14 which is inserted into the body of the patient and is placed at the appropriate location for viewing a desired surgical area. The tubular portion 14 attaches at its proximal end to a handle portion 12 which may be grasped by a surgeon who is conducting the endoscopic procedure. The handle 12 may include a central lumen or channel 13 which receives therethrough one or more cables or other structures which extend to the distal end 16 of tubular portion 14. Handle portion 12 may further include a supplementary channel 15 which intersects with central channel 13 and which may provide another point of entry for other cables, fluids or operative instruments to be placed through the endoscope.

FIG. 1b illustrates the distal end 16 of the endoscope 10. The distal end 16 may be characterized by an outer tube 18 which traverses the length of the tubular portion 14 and connects to the handle portion 12. Placed concentrically within the outer tube 18 may be one or more inner tubes 20.

In FIG. 1b, the gap between inner tube 20 and outer tube 18 forms a space in which one or more light fibers 22 or control wires 24 may be placed. As well understood by those skilled in the art, a plurality of circumferentially spaced light fibers as illustrated in FIG. 1b can be used to illuminate the surgical site. A light source (not shown) can be provided which transmits a desired frequency/wavelength of light through the light fibers as well understood by those skilled in the art. It is also contemplated within the scope of this invention that fluorescence-guided endoscopy can be conducted by the use of an appropriate light source having the ability to deliver light at a pre-selected wavelength. Additionally, the control wires 24 may communicate with a control mechanism (not shown) integrated on the handle portion 12 for manipulating the distal end 16 of the endoscope in a desired direction. The flexible tubular portion 14 coupled with a steerable feature enables the endoscope to be placed within winding bodily passages or other locations difficult to reach within the body. Alternatively, a malleable shaping wire (not shown) may be incorporated in the wall of tube 18 or one of tubes 20 allowing the endoscope 10 to be bent to any desired predetermined shape.

An image sensor 40 may be placed within the central channel defined by inner tube 20. In the configuration shown in FIG. 1b, a cable 26 is used to house the conductors which communicate with the image sensor 40. An intermediate support tube 28 may be placed concentrically outside of cable 26 and concentrically within inner tube 20 to provide the necessary support for the cable 26 as it traverses through the inner channel defined by inner tube 20. In lieu of support tube 28, other well-known means may be provided to stabilize the cable 26 such as clips or other fastening means which may attach to the inner concentric surface of inner tube 20.

A control box 30 may be placed remote from the endoscope 10. The control box 30 contains some of the processing circuitry which is used to process the image signal produced by image sensor 40. Therefore, the imaging device 11 as previously defined would include the processing circuitry within control box 30 and the image sensor 40 located at the distal tip of the endoscope. Control box 30 communicates with image sensor 40 by means of cable 32 which may simply be an insulated and shielded cable which houses therein cable 26. Cable 32 is stabilized with respect to the handle portion 12 by means of a fitting 34 which ensures that cable 32 cannot be inadvertently pushed or pulled within channel 13. Additionally, an additional fitting 35 may be provided to stabilize the entry of a light cable 36 which houses the plurality of light fibers 22.

In an alternative arrangement, the imaging device of this invention can simply be incorporated within the tubular portion 14, and utilize standard connectors directly attached to the tubular portion 14 so that a microendoscope is provided which may be used in combination with the standard surgical devices, as discussed further below with respect to FIGS. 6–16.

Image sensor 40 is illustrated as being a planar and square shaped member. However, the image sensor may be modified to be in a planar and circular shape to better fit within the channel defined by inner tube 20. Accordingly, FIG. 1b further shows an alternate shaped image sensor 40' which is round. A lens group or system 42 may be incorporated at the distal end of the endoscope in order to manipulate the image prior to it being impinged upon the array of pixels on the image sensor 40. This lens system 42 may be sealed at the distal end 16 of the endoscope so that the tubular portion 14 is impervious to fluids entering through the distal end 16. In the configuration of the imaging device 11 in FIGS. 1a and 1b, there are only three conductors which are necessary for providing power to the image sensor 40, and for transmitting an image from the image sensor 40 back to the processing circuitry found within control box 30. Namely, there is a power conductor 44, a grounding conductor 46, and an image signal conductor 48 each of which are hard wired to the image sensor. Thus, cable 26 may simply be a three-conductor 250 ohm cable.

Image sensor 40 can be as small as 1 mm in its largest dimension. However, a more preferable size for most endoscopic procedures would dictate that the image sensor 40 be between 4 mm to 8 mm in its largest dimension. The image signal transmitted from the image sensor through conductor 48 is also herein referred to as a pre-video signal. Once the pre-video signal has been transmitted from image sensor 40 by means of conductor 48, it is received by video processing board 50. Video processing board 50 then carries out all the necessary conditioning of the pre-video signal and places it in a form so that it may be viewed directly on a standard video device, television or standard computer video monitor. The signal produced by the video processing board 50 can be further defined as a post-video signal which can be accepted by a standard video device. As shown in FIG. 1a, a conductor 49 is provided which transmits the post-video signal to an output connector 58 on the exterior surface of control box 30. The cable (not shown) extending from the desired video device (not shown) may receive the post-video signal by means of connector 58. Power supply board 52 may convert incoming power received through power source 54 into the desired voltage. In the preferred imager incorporated in this invention, the power to the imaging device is simply a direct current which can be a 1.5 volt to a 12 volt source. Incoming power from, for example, a wall receptacle, communicates with power supply board 52 by connector 56. Power supply board 52 takes the incoming power source and regulates it to the desired level. Additionally, ground 46 is also shown as extending back to the source of power through connector 56.

FIG. 2a illustrates the invention wherein the imaging device is self-contained entirely within the distal end 16 of the endoscope, and a power source which drives the circuitry within the imaging device may come from a battery 66 housed within handle portion 12.

As shown in FIG. 2b, the video processing board 50 may be placed directly behind image sensor 40. A plurality of pin connectors 62 serve to electrically couple image sensor 40 with video processing board 50 depending upon the specific configuration of image sensor 40, pin connectors 62 may be provided either for structural support only, or to provide a means by which image signals are transmitted between image sensor 40 and board 50. When necessary, one or more supplementary boards 60 may be provided which further contain processing circuitry to process the image signal and present it in a form which may be directly received by a desired video device. The area which is occupied by image sensor 40 may be defined as the profile area of the imaging device and which determines its critical dimensions. Any imaging elements that are found on boards 50 or 60 must be able to be placed on one or more circuit boards which are longitudinally aligned with image sensor 40 along longitudinal axis XX. If the profile area is not critical in terms of limiting the largest sized imaging element within the imaging device, then the additional circuit boards 50 and 60 which are normally placed in line with image sensor 40 can be aligned in an offset manner or may be larger than the profile area of image sensor 40. In the configuration of FIG.

2b, it is desirable that elements 40, 50 and 60 be approximately the same size so that they may fit uniformly within the central channel of the endoscope. Additionally, image sensor 40 may be bonded to lens system 42 in order to provide further structural support to the imaging device II when mounted within the distal end 16.

Referring back to the handle portion 12 in FIG. 2a, an additional channel 64 may be provided in order that a power supply cable 68 may communicate with battery 66. Conveniently, battery 66 may itself be mounted within a well 65 formed in handle portion 12. Cable 68 carries the conductor 44 and ground 46. Cable 68 may intersect with cable 33 within channel 13, cables 68 and 33 extending then to the distal end 16. Cable 33 can be a single conductor cable which transmits the post-video signal to a desired video device. In other words, cable 33 may simply be an insulated and shielded housing for conductor 49 which carries the post-video signal. Because a preferred image sensor of the imaging device 11 may only require a 5 volt power supply, a battery is an ideal power source in lieu of a conductor which would trail the endoscope. Accordingly, the endoscope is made more mobile and easier to handle by eliminating at least one of the trailing cables.

FIG. 3a illustrates yet another arrangement of this invention, wherein the imaging device can be used in conjunction with a standard rod lens endoscope 70. As shown, rod lens endoscope 70 includes a lens train 72 which includes a plurality of highly precise lenses (not shown) which are able to transmit an image from the distal end of the endoscope, to a camera in line with the endoscope. The rod lens endoscope is equipped with a light guide coupling post 74. Light guide post 74 connects to a source of light in the form of a cable 77 having a plurality of fiber optic strands (not shown) which communicate with a source of light (not shown). The most common arrangement of the rod lens endoscope also includes a "C" or "V" mount connector 78 which attaches to the eyepiece 76. The "C" or "V" mount attaches at its other end to a camera group 80. The camera group 80 houses one or more of the elements of the imaging device. In this embodiment, the small size of the imaging device is not a critical concern since the imaging device is not being placed at the distal end of the endoscope. However, the incorporation of the imaging device in a housing which would normally hold a traditional camera still provides an advantageous arrangement. As shown, the camera group 80 may include a housing 82 which connects to a power/video cable 86. Fitting 87 is provided to couple cable 86 to the interior elements of the camera group 80 found within housing 82. FIG. 3a illustrates an arrangement of the imaging device 11 wherein the image sensor 40 is placed by itself within the housing 82 and the processing circuitry of the imaging device can be positioned in a remote control box as shown in FIG. 1 a. Accordingly, only three conductors 44, 46 and 48 are necessary for providing power to the image sensor 40 and for transmitting the pre-video signal to the control box. Alternatively, as shown in FIG. 3b, the entire imaging device 11 may be incorporated within camera group 80, each of the elements of the imaging device being placed in the stacked arrangement similar to FIG. 2b. As discussed above, size is not as much of a concern in the embodiment of FIG. 3a and 3b since the camera group housing 82 is much larger than the distal tip of the endoscope of FIGS. 1a and 2a.

FIG. 3c also illustrates the use of a battery 66 which provides source of power to the imaging device in either FIG. 3a or 3b . In this arrangement, housing 82 is altered to include a battery housing 69 which houses the battery 66 therein. Battery housing 69 may include a very small diameter channel which may allow conductor 48 or 49 to communicate directly with the processing circuitry or video device, respectively. It will also be understood that the embodiment in FIG. 1a may incorporate the use of a battery 66 as the source of power. Thus, handle 12 in FIG. 1a may be altered in the same way as housing 82 to allow a battery to be attached to the handle portion 12.

FIG. 4 is a schematic diagram illustrating one way in which the imaging device 11 may be constructed. As illustrated, the image sensor 40 may include the timing and control circuits on the same planar structure. Power is supplied to image sensor 40 by power supply board 52. The connection between image sensor 40 and board 52 may simply be a cable having two conductors therein, one for ground and another for transmitting the desired voltage. These are illustrated as conductors 44 and 46. The output from image sensor 40 in the form of the pre-video signal is input to video processor board 50 by means of the conductor 48. In the configuration of FIG. 4, conductor 48 may simply be a 50 ohm conductor. Power and ground also are supplied to video processing board 50 by conductors 44 and 46 from power supply board 52. The output signal from the video processor board 50 is in the form of the post-video signal and which may be carried by conductor 49 which can also be a 50 ohm conductor.

In the first arrangement illustrated in FIG. 1a, cable 32 can be used to house conductors 44, 46 and 48. In the arrangement shown in FIG. 2a, cable 33 can be used to house conductor 49 by itself when a battery power source is used, or alternatively, cable 33 may house conductors 44, 46 and 49 if the arrangement of FIG. 2a utilizes a power source from board 52.

Optionally, a supplementary processing board 60 may be provided to further enhance the pre-video signal. As shown in FIG. 4, the supplementary board 60 may be placed such that the pre-video signal from image sensor 40 is first sent to the supplementary board and then output to the video processor board 50. In this case, the output from board 50 can be carried along conductor 51. This output can be defined as an enhanced pre-video signal. Furthermore, the post-video signal from video processor board 50 may return to the supplementary board 60 for further processing, as further discussed below. The conductor used to transmit the post-video signal back to the supplementary board is shown as conductor 59. The power supply board 52 may also provide power to the supplementary board in the same manner as to image sensor 40 and board 50. That is, a simple hard-wired connection is made onto the supplementary board for the ground and voltage carrying conductors. As discussed above, image sensor 40 may be placed remotely from boards 50 and 60. Alternatively, image sensor 40, and boards 50 and 60 each may be placed within the distal end of the endoscope.

Although FIG. 4 illustrates the image sensor and the timing and control circuits being placed on the same planar structure, it is possible to separate the timing and control circuits from the pixel array and place the timing and control circuits onto video processing board 50. The advantage in placing the timing and control circuits on the same planar structure as the image sensor is that only three connections are required between image sensor 40 and the rest of the imaging device, namely, conductors 44, 46 and 48. Additionally, placing the timing and control circuits on the same planar structure with the pixel array results in the pre-video signal having less noise. Furthermore, the addition of the timing and control circuits to the same planar structure carrying the image sensor only adds a negligible amount of size to one dimension of the planar structure. If the pixel array is to be the only element on the planar structure, then additional connections must be made between the planar structure and the video processing board 50 in order to transmit the clock signals and other control signals to the pixel array. For example, a ribbon-type cable (not shown) or a plurality of 50 ohm coaxial cables (not shown) must be used in order to control the downloading of information from the pixel array. Each of these additional connections would be hard wired between the boards.

FIG. 4a is a more detailed schematic diagram of image sensor 40 which contains an array of pixels 90 and the timing and control circuits 92. One example of a pixel array 90 which can be used within the invention is similar to that which is disclosed in U.S. Pat. No. 5,471,515 to Fossum, et al., said patent being incorporated by reference herein. More specifically, FIG. 3 of Fossum, et al. illustrates the circuitry which makes up each pixel in the array of pixels 90. The array of pixels 90 as described in Fossum, et al. is an active pixel group with intra-pixel charged transfer. The image sensor made by the array of pixels is formed as a monolithic complementary metal oxide semiconductor integrated circuit which may be manufactured in an industry standard complementary metal oxide semiconductor process. The integrated circuit includes a focal plane array of pixel cells, each one of the cells including a photo gate overlying the substrate for accumulating the photo generated charges. In broader terms, as well understood by those skilled in the art, an image impinges upon the array of pixels, the image being in the form of photons which strike the photo diodes in the array of pixels. The photo diodes or photo detectors convert the photons into electrical energy or electrons which are stored in capacitors found in each pixel circuit. Each pixel circuit has its own amplifier which is controlled by the timing and control circuitry discussed below. The information or electrons stored in the capacitors is unloaded in the desired sequence and at a desired frequency, and then sent to the video processing board 50 for further processing.

Although the active pixel array disclosed in U.S. Pat. No. 5,471,515 is mentioned herein, it will be understood that the hybrid CCD/CMOS described above, or any other solid state imaging device may be used wherein timing and control circuits can be placed either on the same planar structure with the pixel array, or may be separated and placed remotely. Furthermore, it will be clearly understood that the imaging device disclosed herein is not limited to an image sensor as specifically disclosed in the U.S. Pat. No. 5,471,515, but encompasses any image sensor which may be configured for use in conjunction with the other processing circuitry which makes up the imaging device of this invention.

The timing and control circuits 92 are used to control the release of the image information or image signal stored in the pixel array. In the image sensor of Fossum, et al., the pixels are arranged in a plurality of rows and columns. The image information from each of the pixels is first consolidated in a row by row fashion, and is then downloaded from one or more columns which contain the consolidated information from the rows. As shown in FIG. 4a, the control of information consolidated from the rows is achieved by latches 94, counter 96, and decoder 98. The operation of the latches, counter and decoder is similar to the operation of similar control circuitry found in other imaging devices. That is, a latch is a means of controlling the flow of electrons from each individual addressed pixel in the array of pixels. When a latch 94 is enabled, it will allow the transfer of electrons to the decoder 98. The counter 96 is programmed to count a discrete amount of information based upon a clock input from the timing and control circuits 92. When the counter 96 has reached its set point or overflows, the image information is allowed to pass through the latches 94 and be sent to the decoder 98 which places the consolidated information in a serial format. Once the decoder 98 has decoded the information and placed it in the serial format, then the row driver 100 accounts for the serial information from each row and enables each row to be downloaded by the column or columns. In short, the latches 94 will initially allow the information stored in each pixel to be accessed. The counter 96 then controls the amount of information flow based upon a desired time sequence. Once the counter has reached its set point, the decoder 98 then knows to take the information and place it in the serial format. The whole process is repeated, based upon the timing sequence that is programmed. When the row driver 100 has accounted for each of the rows, the row driver reads out each of the rows at the desired video rate.

The information released from the column or columns is also controlled by a series of latches 102, a counter 104 and a decoder 106. As with the information from the rows, the column information is also placed in a serial format which may then be sent to the video processing board 50. This serial format of column information is the pre-video signal carried by conductor 48. The column signal conditioner 108 places the column serial information in a manageable format in the form of desired voltage levels. In other words, the column signal conditioner 108 only accepts desired voltages from the downloaded column(s).

The clock input to the timing and control circuits 92 may simply be a quartz crystal timer. This clock input is divided into many other frequencies for use by the various counters. The run input to the timing and control circuit 92 may simply be an on/off control. The default input can allow one to input the pre-video signal to a video processor board which may run at a frequency of other than 30 hertz. The data input controls functions such as zoom. At least for a CMOS type active pixel array which can be accessed in a random manner, features such as zoom are easily manipulated by addressing only those pixels which locate a desired area of interest by the surgeon.

A further discussion of the timing and control circuitry which may be used in conjunction with an active pixel array is disclosed in U.S. Pat. No. 5,471,515 and is also described in an article entitled "Active Pixel Image Sensor Integrated With Readout Circuits" appearing in *NASA Tech Briefs*, October 1996, pp. 38 and 39. This particular article is also incorporated by reference.

Once image sensor 40 has created the pre-video signal, it is sent to the video processing board 50 for further processing. At board 50, as shown in FIG. 4b, the pre-video signal is passed through a series of filters. One common filter arrangement may include two low pass filters 114 and 116, and a band pass filter 112. The band pass filter only passes low frequency components of the signal. Once these low frequency components pass, they are then sent to detector 120 and white balance circuit 124, the white balance circuit distinguishing between the colors of red and blue. The white balance circuit helps the imaging device set its normal, which is white. The portion of the signal passing through low pass filter 114 then travels through gain control 118 which reduces the magnitude or amplitude of this portion to a manageable level. The output from gain control 18 is then fed back to the white balance circuit 124. The portion of the signal traveling through filter 116 is placed through the processor 122. In the processor 122, the portion of the signal carrying the luminance or non-chroma is separated and sent to the Y chroma mixer 132. Any chroma portion of the signal is held in processor 122.

Referring to the output of the white balance circuit 124, this chroma portion of the signal is sent to a delay line 126 where the signal is then further reduced by switch 128. The output of switch 128 is sent through a balanced modulator 130 and also to the Y chroma mixer 132 where the processed chroma portion of the signal is mixed with the processed non-chroma portion. Finally, the output from the Y chroma mixer 132 is sent to the NTSC/PAL, encoder 134, commonly known in the art as a "composite" encoder. The composite frequencies are added to the signal leaving the Y chroma mixer 132 in encoder 134 to produce the post-video signal which may be accepted by a television.

Referring back to FIG. 4, it further illustrates supplementary board 60 which may be used to digitally enhance or otherwise further condition the pre-video signal produced from image sensor 40. For example, digital enhancement can brighten or otherwise clarify the edges of an image viewed on a video screen. Additionally, the background images may be removed thus leaving only the foreground images or vice versa. The connection between image sensor 40 and board 60 may simply be the conductor 48 which may also transfer the pre-video signal to board 50. Once the pre-video signal has been digitally enhanced on supplementary board 60, it is then sent to the video processor board 50 by means of another conductor 51. The pre-video signal is an analog signal. The digitally enhanced pre-video signal may either be a digital signal or it may be converted back to the analog domain prior to being sent to board 50.

In addition to digital enhancement, supplementary board 60 may further include other circuitry which may further condition the post-video signal so that it may be viewed in a desired format other than NTSC/PAL. As shown in FIG. 4, intermediate conductor 59 may transmit the signal output from Y chroma mixer 132 back to the supplementary board 60 where the signal is further encoded for viewing in a particular format. One common encoder which can be used includes an RGB encoder 154. The RGB encoder separates the signal into three separate colors (red, green and blue) so that the surgeon may selectively choose to view only those images containing one or more of the colors. Particularly in tissue analysis where dyes are used to color the tissue, the RGB encoder may help the surgeon to identify targeted tissue.

The next encoder illustrated in FIG. 4 is a SVHS encoder 156 (super video home system). This encoder splits or separates the luminance portion of the signal and the chroma portion of the signal prior to entering the video device. Some observers believe that a cleaner signal is input to the video device by such a separation which in turn results in a more clear video image viewed on the video device. The last encoder illustrated in FIG. 4 is a VGA encoder 158 which enables the signal to be viewed on a standard VGA monitor which is common to many computer monitors.

One difference between the arrangement of image sensor 40 and the outputs found in FIG. 3 of the Fossum, et al. patent is that in lieu of providing two analog outputs [namely, VS out (signal) and VR out (reset)], the reset function takes place in the timing and control circuitry 92. Accordingly, the pre-video signal only requires one conductor 48.

FIGS. 5a–5e illustrate in more detail one example of circuitry which may be used in the video processing board 50 in order to produce a post-video signal which may be directly accepted by a video device such as a television. The circuitry disclosed in FIGS. 5a–5e is very similar to circuitry which is found in a miniature quarter-inch Panasonic camera, Model KS-162. It will be understood by those skilled in the art that the particular arrangement of elements found in FIGS. 5a–5e are only exemplary of the type of video processing circuitry which may be incorporated in order to take the pre-video signal and condition it to be received by a desired video device.

Figure 5A:
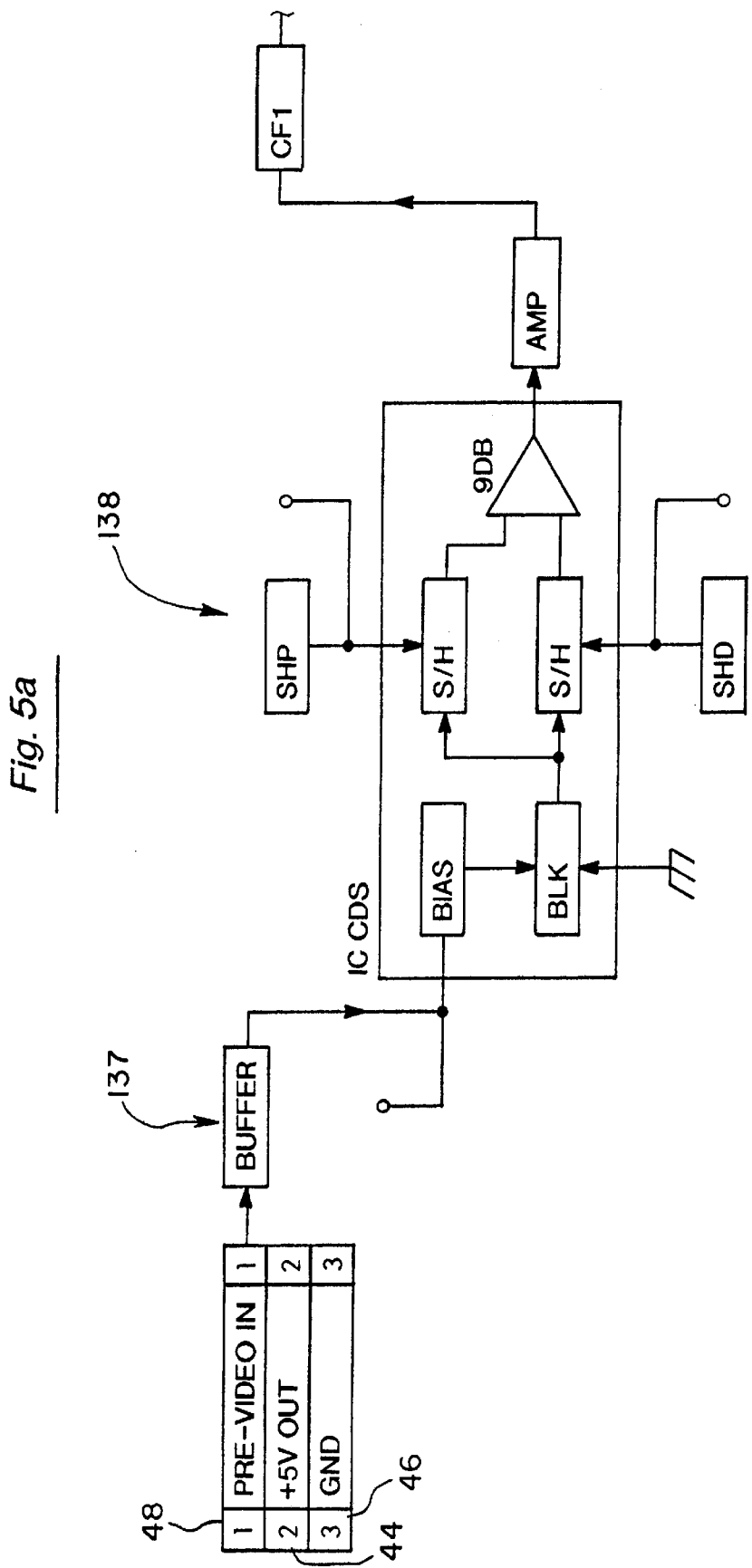
FIGS. 5a–5e are schematic diagrams that illustrate an example of specific circuitry which may be used to make the imaging device.

As shown in FIG. 5a, 5 volt power is provided along with a ground by conductors 44 and 46 to board 50. The pre-video signal carried by conductor 48 is buffered at buffer 137 and then is transferred to amplifying group 138. Amplifying group 138 amplifies the signal to a usable level as well as achieving impedance matching for the remaining circuitry.

Figure 5B:
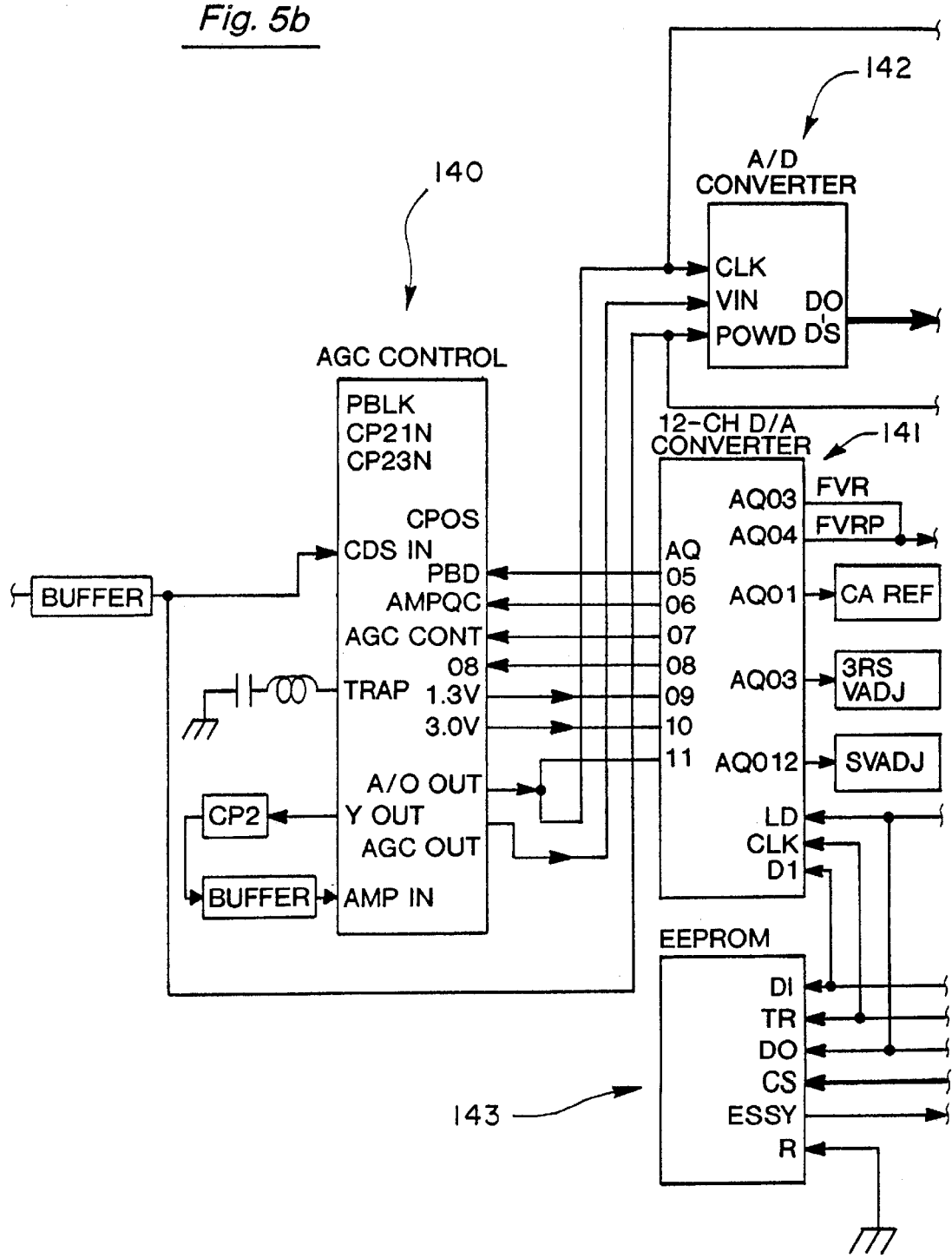

The next major element is the automatic gain control 140 shown in FIG. 5b. Automatic gain control 140 automatically controls the signal from amplifying group 138 to an acceptable level and also adds other characteristics to the signal as discussed below. More specifically, automatic gain control 140 conditions the signal based upon inputs from a 12 channel digital to analog converter 141. Converter 141 retrieves stored information from EEPROM (electrically erasable programmable read only memory) 143. EEPROM 143 is a non-volatile memory element which may store user information, for example, settings for color, tint, balance and the like. Thus, automatic gain control 140 changes the texture or visual characteristics based upon user inputs. The signal leaving the automatic gain control 140 is an analog signal until being converted by analog to digital converter 142.

Figure 5C:
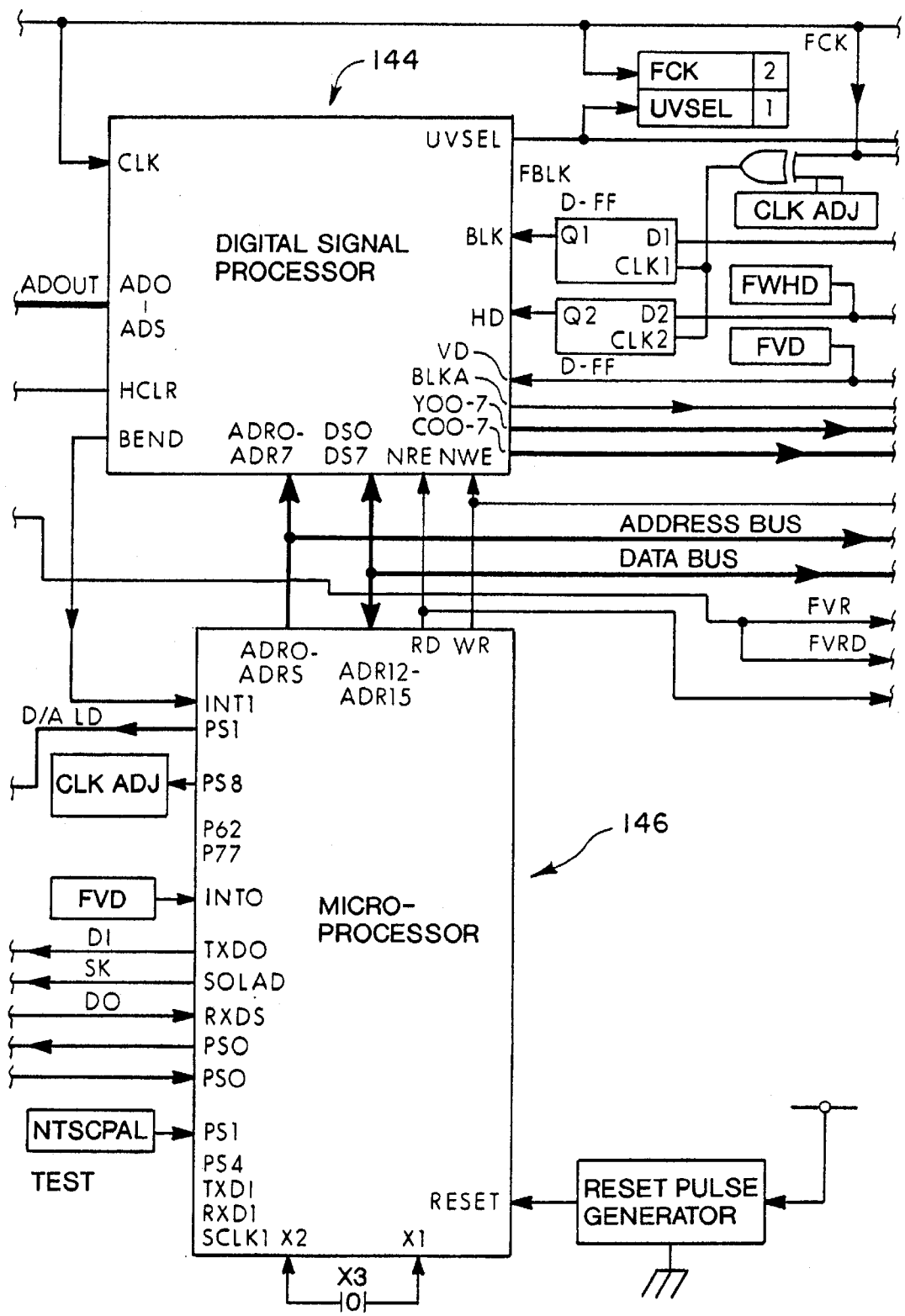

Digital signal processor 144 of FIG. 5c further processes the converted signal into a serial type digital signal. One function of the microprocessor 146 is to control the manner in which digital signal processor 144 sorts the digital signals emanating from converter 142. Microprocessor 146 also controls analog to digital converter 142 in terms of when it is activated, when it accepts data, when to release data, and the rate at which data should be released. Microprocessor 146 may also control other functions of the imaging device such as white balance. The microprocessor 146 may selectively receive the information stored in the EEPROM 143 and carry out its various commands to further control the other elements within the circuitry.

Figure 5D:
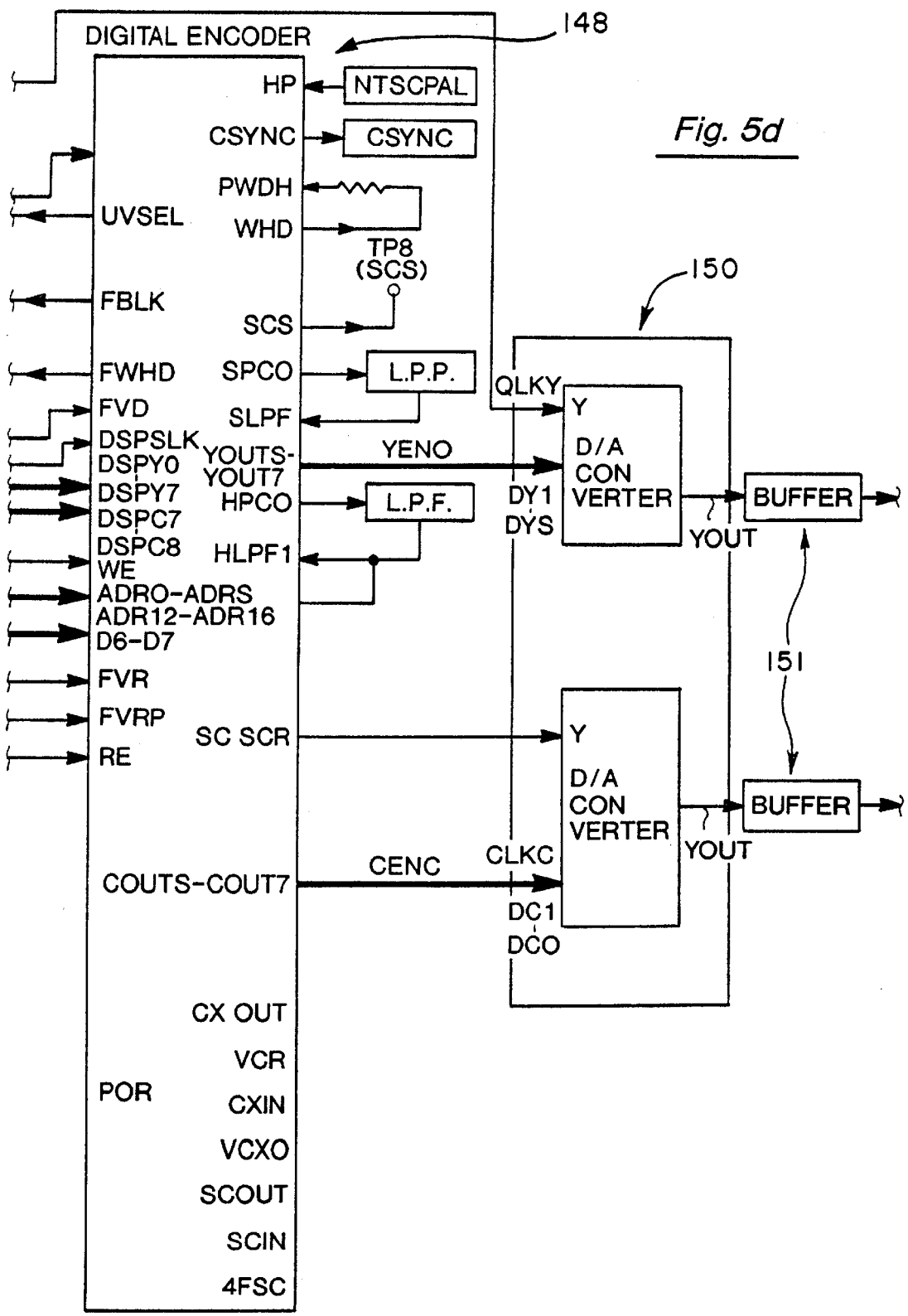

After the signal is processed by digital signal processor 144, the signal is sent to digital encoder 148 illustrated in FIG. 5d. Some of the more important functions of digital encoder 148 are to encode the digital signal with synchronization, modulated chroma, blanking, horizontal drive, and the other components necessary so that the signal may be placed in a condition for reception by a video device such as a television monitor. As also illustrated in FIG. 5d, once the signal has passed through digital encoder 148, the signal is reconverted into an analog signal through digital to analog converter 150.

Figure 5E:
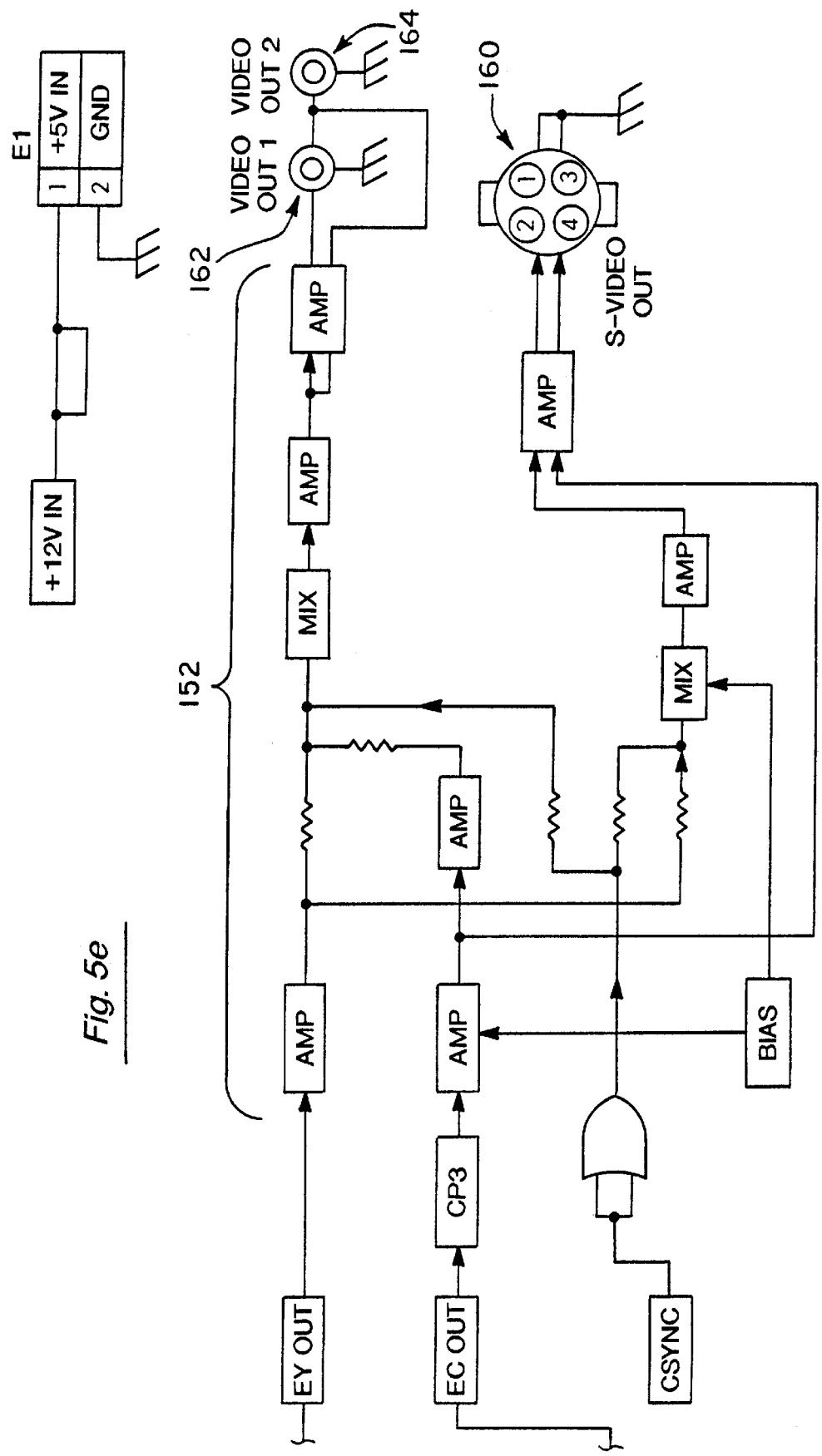

This reconverted analog signal is then buffered at buffers 151 and then sent to amplifier group 152 of FIG. 5e which amplifies the signal so that it is readily accepted by a desired video device. Specifically, as shown in FIG. 5e, one SVHS outlet is provided at 160, and two composite or NTSC outlets are provided at 162 and 164, respectively.

From the foregoing, it is apparent that an entire imaging device may be incorporated within the distal tip of an endoscope, or may have some elements of the imaging device being placed in a small remote box adjacent to the endoscope. Based upon the type of image sensor used, the profile area of the imaging device may be made small enough to be placed into an endoscope which has a very small diameter tube. Additionally, the imaging device may be placed into the channels of existing endoscopes to provide additional imaging capability without increasing the size of the endoscope. The imaging device may be powered by a standard power input connection in the form of a power cord, or a small lithium battery may be used.

FIGS. 6–16 illustrate various medical instruments which may incorporate the imaging device of this invention. In order to be combined with the medical instruments described below, the imaging device may simply be incorporated within a tubular structure without the need for providing any type of handle or other means to grip the imaging device. Accordingly, the imaging device can be housed within tubular portion 14 as discussed above with respect to FIGS. 1a and 1b, and the proximal end of the tubular structure can include the standard connectors allowing the imaging device to be connected directly to a video display device, or for connection to the control box 30.

As shown in FIG. 6, tubular portion 14 is of any desired length to be incorporated within the desired surgical instrument, such as Jackson grasping forceps 230. As shown in FIG. 6, the proximal end of the tubular portion 14 may be adapted for direct connection to a video port on a video device, such as a laptop computer 229 shown in FIG. 7. Alternatively, the proximal end of tubular portion 14 can be connected to the control box 30 if circuitry in the image device is configured such that control box 30 is desired. As with cable 32 which is used within the endoscope shown in FIG. 1a, outer tube branches 18 may also include insulation and shielding to ensure integrity of the image signal which is transmitted either directly to a video display, or to the control box 30. One of the branches 18 at the proximal end of tubular portion 14 includes light guide fitting/connector 25 which allows the imaging device to communicate with a light source 228.

As shown in FIG. 7, an intermediate cable/conductor 59 interconnects the laptop computer 229 to the video output connector 58, and cable/conductor 61 interconnects power connector 56 to a source of power (not shown).

There is essentially no limit as to the length of the tubular portion 14. One section of the tubular portion 14 could be made sterile and have a sufficient length which enabled it to extend out of the sterile field of the surgical area and then connect to the appropriate video control or light sources. The tubular portion 14 can be made of more rigid materials such as stainless steel, aluminum, or even semi-rigid plastic tubing made by companies such as the Polygon Company of Walkerton, Ind. Polygon tubing is a material made of a composite plastic and is structurally as strong as many metal materials. Preferably, however, the tubular portion 14 may be made of plastics which are thin-walled and flexible. Using such a flexible material allows for the imaging device to be both flexible and steerable for use with many different types of surgical instruments. Preferable materials for making the tubular portion 14 flexible and steerable include various formulations of teflon®, polyethylene, and polypropylene. Furthermore, if the tubular portion 14 is made flexible, it can conform to the sharp turns and twists that it may encounter within the body on the path to the desired surgical site.

In addition to providing a sterile tubular portion 14 extending a desired length to ensure that it extends away from the sterile field, a thin-walled drape (not shown) could be used which is sterile and covers any wiring or cables which are exposed near the proximal end of the tubular portion 14 and which may still be in the sterile field. Although not illustrated, it is well understood by those skilled in the art to use a drape which isolates non-sterile components from the sterile field.

The first application of the microendoscope is illustrated in FIGS. 6 and 7. As shown, the microendoscope may be used with modified Jackson grasping forceps 230. The particular grasping forceps 230 illustrated in FIG. 6 is characterized by an instrument channel 232 which may receive therethrough a pair of elongate grasping tines 234. The grasping tines 234 terminate at the proximal end by forming a single tine rod 235. Grasping tines 234 may be slid inwardly or outwardly within instrument channel 232 by the scissor action of first member 240 and second member 242. The first and second members 240 and 242 connect at pivot point 244. The distal end of second member 242 includes a push link 246 attached thereto at one end by means of pin 250. The other end of push link 246 is connected to bracket 248 by means of pin 252. As rings 256 and 258 of members 242 and 240 are pressed together by the fingers of a surgeon, first member 240 will cause the grasping tines 234 to be moved in a rearward or proximal direction such that the normally separated or open distal ends of tines 234 are pressed or drawn together by their proximal movement into the instrument channel 232. When it is desired to have the tines 234 protrude from the instrument channel 232, rings 256 and 258 are again separated. The forceps are able to grasp a foreign object by the open-close action of the tines 234. Conveniently, tightening knob 254 may be provided so that first member 240 may be positioned at a desired location along tine rod 235. The particular positioning of first member 240 along tine rod 235 enables the grasping tines 234 to protrude a desired distance beyond the distal end of instrument channel 232.

The grasping forceps 230 are modified to include an endoscope tube 236 which receives the tubular portion 14. The tube 236 may be welded or glued alongside channel 232, or attached by other well-known means. Conveniently, the endoscope tube 236 may include a tightening knob or adjustment member 238 to control the extent to which the distal end 16 protrudes beyond the distal end of the endoscope tube 236. Placement of the microendoscope directly alongside the forceps enables the microendoscope to view the tines as they are manipulated to grasp the foreign object. The forward or distal placement of the microendoscope also enables it to view the path of insertion into the patient.

As shown in FIG. 7, the Jackson grasping forceps are inserted into the patient P to remove a foreign object O which can be viewed on the screen of the video control device 229. From the surgery being performed in FIG. 7, a foreign object such as a coin may be removed from the lungs or trachea of the patient P by means of the Jackson grasping forceps 230. In the past, an instrument such as a full-sized Jackson grasping forceps could not be introduced simultaneously with an endoscope because the trachea or throat of the patient could not accommodate the simultaneous introduction of both the forceps and the endoscope. Therefore, this procedure previously had to be conducted without the surgeon being able to visualize the Jackson grasping forceps as it was introduced into and through the path in the patient's body prior to reaching the surgical site under investigation. Because of the small size of the tubular portion 14, the addition of endoscope tube 236 makes it possible for the Jackson grasping forceps to have the integral imaging capability. In the operation depicted in FIG. 7, the Jackson grasping device is the preferred surgical instrument since large objects such as coins require removal by tines of substantial size and strength as found only with such forceps. In other words, smaller forceps which may be introduced through a channel of standard endoscopes do not have the grasping strength or size to hold a relatively large foreign object such as a coin.

FIGS. 8 and 9 illustrate the microendoscope being used in conjunction with a stent placement catheter 290. One common procedure used to dilate or expand a blocked artery A is the introduction of a stent which is used to force open the blockage B. As shown in FIG. 8, a stent placement catheter assembly 290 may include a catheter tube 292 which is used to transfer a stent coil 294 to the blockage B. The stent coil 294 is wrapped around the exterior walls of the catheter tube 292. A pair of control wires 296 and 298 may connect to the opposite ends of the stent coil 294 at junctions 300 and 302, respectively. Retainers 299 may be used to secure the control wires 296 and 298 to the catheter tube 292. Alternatively, channels (not shown) formed within the walls of the tube 292 may be used to secure the control wires. In prior procedures, the small size of many arteries A prevented the introduction of an endoscope within the artery itself. Accordingly, exact placement of the stent 294 as viewed within the artery was not possible. Because of the small size of the microendoscope, it can be placed inside the catheter tube 292 so to provide the surgeon a view of the interior wall of the artery.

In operation, the distal end 16 of the tubular portion 14 may protrude beyond the distal end of the catheter tube 292 in order to provide an image to the surgeon as the stent placement catheter is traversed through the artery or other bodily passages on the route to the artery. As shown in FIG. 9, once the stent placement catheter has been introduced into the blockage B, the microendoscope may be removed from within the stent placement catheter and the stent coil may be activated to dilate the blockage B. One popular procedure for activating the stent coil 294 is to make the stent from a material such as Nitronol which will remain expanded when activated within the body. Nitronol is a material which is very sensitive to changes in temperature. A low electric current may be introduced through the first and second control wires 296 and 298 in order to heat and, therefore, activate the stent coil 294 so that it uncoils or unravels within the blockage B. Furthermore, the electric current introduced through control wires 296 and 298 will cause the forked ends of junctions 300 and 302 to open thus enabling the control wires to be separated from the opposite ends of the stent coil 294. FIG. 9 illustrates the control wires 296 and 298 being removed after the appropriate electric current has expanded the stent coil 294 and has caused the release of junctions 300 and 302 from the opposite ends of the stent coil 294. After the stent coil has been activated, the catheter may be placed adjacent the coil and the microendoscope may again protrude from the distal end of the catheter enabling the microendoscope to again view the stent to ensure its proper placement.

FIGS. 10 and 11 illustrate another application of the microendoscope with a surgical instrument. As shown in FIG. 10, a very small diameter over-tube tissue separating device 304 is provided over outer tube 18 which is characterized by a guide tube 306 which receives the microendoscope. An extension 307 is formed on the distal end of the guide tube 306 to provide a desired separation between the microendoscope and a tissue contacting member. In FIG. 10, the tissue contacting member is in the form of a separating bead 308. In use, the microendoscope may be introduced into a bodily passage simultaneously with the over-tube separator 304 wherein the separating bead 308 can separate linings of tissue or other discrete delineations between tissue types so that a subsequent surgical procedure can take place at the location of the separated tissues. Because of the extremely small size of the microendoscope, the separating bead 308 can be used in the most delicate separating procedures. The guide tube 306 is preferably rigid and may extend any desired length depending upon the particular bodily passage within which the separator 304 is to be introduced.

FIG. 11 illustrates one modification of the over-tube separator 304. As shown in FIG. 11, the over-tube device may take the form of an over-tube dissector 310 which also includes a guide tube 312 over outer tube 18 and an extension 313. In lieu of the separating bead 308, the extension 313 may have attached thereto a dissecting hook 316 which can be used to separate, cut, or otherwise manipulate tissue in a desired location. As further shown in FIG. 11, the distal end 16 may protrude beyond the distal end of the guide tube 312. Alternatively, as shown in FIG. 10, an adequate visual image of the area under investigation may be achieved by having the distal end 16 positioned flush with the distal end of the guide tube 306. Although not illustrated, the over-tube dissector could also include an electrode positioned adjacent to or in lieu of the separating bead 308 or hook 316. Such an electrode could be charged with an electric current to fulgerate tissue at a desired area.

In yet another application, the microendoscope may be used in conjunction with a balloon catheter 320. The balloon catheter 320 shown in FIG. 12 is of a type used within very small bodily passages such as the urethra or the like. The balloon catheter 320 may include an elongate guide tube 322 having a distal end 323 which may be non-steerable, or steerable by guide wires (not shown) and a steering unit (not shown) which controls the guide wires as understood by those skilled in the art. The free or proximal end of air inflation port 324 connects to stop cock 328 which in turn connects to syringe 330. A very small diameter air inflation line (not shown) may be formed interiorly of guide tube 322 and connect between port 324 and openings 334, shown in FIG. 13. When the plunger 332 of the syringe is depressed, air is forced through air inflation port 324, through the small inflation line (not shown) and through openings 334 to inflate the balloon 336. Stop cock 328 may be positioned to prevent the back flow of air into the syringe 330 thus keeping the balloon inflated. As also shown in FIG. 12, guide tube 322 may further include its own stop cock 326 positioned at the proximal end thereof in order that the guide tube 322 may also introduce liquids or gas simultaneously with the endoscope. Supply tubes (not shown) can supply the appropriate liquids or gas through stop cock 326.

The sequential operation of the balloon catheter will now be explained with reference to FIGS. 13–15. First, the microendoscope is inserted through the guide tube 322. The distal end 16 may protrude beyond the distal end 323 of the guide tube 322 as shown in FIG. 13. The catheter is then inserted into the body of a patient. As the balloon catheter is traversed through the desired bodily passage, the microendoscope can provide a continuous image of the path of traversal. When the distal end of the balloon catheter reaches its desired destination, balloon 336 may be inflated as illustrated in FIG. 14. As shown in FIG. 15, the microendoscope may then be withdrawn back through the guide tube 322. The desired surgical procedure may then take place by the introduction of a desired instrument through the guide tube 322.

In yet another application, the microendoscope may be used in conjunction with an endotracheal intubation device 340. The intubation device 340 shown in FIG. 16 is a standard type used for intubation in all different types of medical procedures to include trauma procedures. The endotracheal intubation device 340 illustrated in FIG. 16 is one example of an endotracheal intubation device such as manufactured by Mallinckrodt. The intubation device 340 is characterized by a semi-rigid endotracheal tube 342, an open distal end 344, an adjacent side opening 346, and a balloon 348, which communicates with inflation tube 350. The distal end of inflation tube 350 is sealed within the side wall of tube 342, and the proximal end of inflation tube 350 separates from the proximal end of tube 342. An inflation fitting 352 communicates with a source of air (not shown) to inflate the balloon 348 the desire amount. A supporting flange 354 is provided at the proximal end of tube 342.

In accordance with the invention, a centering tube 356 and handle 360 are provided. The purpose of the centering tube 356 is to allow fluids or gas to pass through peripheral channels 357 formed within the centering tube 356, as shown in FIG. 16a, and to be delivered to the patient as necessary. The centering tube 356 has a distal tip 358 which can be sized to just fit within intubation tube 342. A luer lock/fitting 362 connects to the proximal end of handle 360. Tube combination 364 communicates through luer lock 362 with centering tube 356. Tube combination 364 can have one tube dedicated for communicating with the peripheral channels formed in centering tube 356, while the other tube within tube combination 364 can communicate with the central opening or lumen within centering tube 356. One dedicated tube in tube combination 364 delivers a desired fluid or gas to the peripheral channels 357. The distal end 16 of tubular portion 14 is inserted through the other tube of tube combination 364, and the distal end 16 is slid through the central opening within centering tube 356 to reside adjacent and just beyond distal tip 358. Then, the centering tube 356 is inserted through endotracheal tube 342 which allows a user to view the insertion of the endotracheal intubation device during an intubation procedure and to deliver the necessary fluid or gas during intubation. Because of the extremely small size of tubular portion 14, and the small size of centering tube 356, means are provided for visualizing insertion of the endotracheal intubation device, along with provision of necessary fluids/gas as intubation is conducted. These advantages are all achieved without unnecessarily restricting the flexibility of intubation tube 342. With the use of a standard endoscope through intubation tube 342, the size of the endoscope makes intubation tube 342 unnecessarily stiff, which can result in additional patient trauma as the intubation procedure is conducted.

In yet another application, an entry trochar 400 may incorporate the imaging device of this invention to form yet another combination of the imaging device of this invention with a hand held instrument. As shown in FIGS. 17 and 18, an entry trochar 400 is provided which may be used to create an entry point for conducting an endoscopic procedure, or other type of invasive surgical procedure. As understood by those skilled in the art, a trochar is a device which forms an opening in the tissue of the patient and allows other instruments to be inserted through the trochar in order to perform a desired procedure. The entry trochar 400 includes a cylindrical tube 402 having a main trochar port 404 attached at the proximal end thereof. The main port 404 may include one or more side ports, such as side port 406 which may used to deliver fluids or gas to the surgical site along cylindrical tube 402. For purposes of the present invention, side port 408 is also included which serves as the means for connecting the imaging device to an external power source, video equipment and the like. As shown, side port 408 is in the form of a four-pin connector. Tube 402 has a hollow core defined by cylindrical inner surface 410. As shown in FIG. 18, cylindrical tube 402 may have a longitudinal channel 411 formed therein which carries a wire bundle 412. Bundle 412 communicates with the imaging device at the distal end of the trochar, as further discussed below.

The distal portion or tip of the trochar 400 is in the form of a tubular imaging section 418 which comprises a tubular member 420 of the same construction as cylindrical tube 402. Accordingly, Section 418 also has a cylindrical inner surface 419 and a longitudinal channel 421 which aligns with channel 411. The distal end of tubular member 420 includes the trochar cutting tip 422 which is used to penetrate the tissue of the patient for entry to the desired surgical site. Mounted within tubular member 420 are the imaging elements of the imaging device, and the components to provide light for the imaging device. Specifically, a light source 424 is mounted within tubular member 420. The light source 424 may be a white light laser diode, or other well-known light sources which are of sufficiently small size which can be mounted within the tubular member 420. The light source 424 produces a beam of light 426 which impinges upon a tightly grouped bundle of light fibers 430, which may be held together by a ferrule 428 or other well-known components. FIG. 18 illustrates the tubular member 420 as it is rotated back upon the cylindrical tube 402 as by micro hinge 416. A control wire 414 may extend through channel 411 adjacent wire bundle 412, and be secured at its distal end 415 to tubular member 420, enabling the imaging section 418 to be rotated either in the closed position, shown in FIG. 17, such that imaging section 418 aligns longitudinally with cylindrical tube 402, or so that imaging section 418 may be rotated back as shown in FIG. 18. When the imaging section 418 has been rotated as shown in FIG. 18, the viewing end 432 of the imaging section 418 is exposed. An image sensor 434 and an objective lens 436 are also mounted within the imaging section 418 adjacent the viewing end 432. The image sensor 434 is the same as described above with respect to the imaging device as shown and described with respect to FIGS. 1 and 2. As shown in FIGS. 18 and 19, the light fibers 430 extend toward the viewing end 432 and may be placed peripherally around the viewing end 432 to provide the best dispersed light. A washer-shaped member 433 is mounted at the viewing end 432 and provides means for spacing the fibers 430 in the circumferential manner as well as centering the objective lens 436. In accordance with the imaging device described above, the image sensor 434 includes a power conductor 438, a grounding conductor 440, and an image signal conductor 442 which communicates with a remote control box 30 via pin connector 408. The plurality of conductors 438, 440 and 442 are housed within wire bundle 412 and are separated as needed within tubular member 420. Alternatively, in lieu of a control box 30, a plurality of circuit boards (not shown) could be mounted within imaging section 418, in the same manner as described above with respect to FIG. 2b. As also shown, a power conductor 444 provides power to light source 424, power conductor 444 also being housed within wire bundle 412.

In a modified configuration of the entry trochar, in lieu of a hinged imaging section, the image sensor alone could be the element which hinges away from the longitudinal axis of the cylindrical tube 402. In accordance therewith, the image sensor 434 could be encapsulated within a protective covering, and simply hinged to the exterior surface of the cylindrical tube 402. When the trochar was to be inserted within a patient, the image sensor would be folded back and would lie tightly against the exterior surface of the cylindrical tube 402 and, further, a small notch or cut-out portion could be formed in the exterior surface of the cylindrical tube 402 in order to receive the image sensor 434. When it is necessary to view the surgical site, the image sensor could be deployed by rotating the image sensor away from the cylindrical tube 402 and having it face the surgical site. In order to obtain stereoscopic vision of the surgical site, a pair of image sensors could rotatably or hingeably mounted to the cylindrical tube 402 in a spaced apart relationship. The distal end or tip of the trochar would include the cutting tip 422 permanently affixed thereto.

In use, a surgeon would make entry in the body of the patient through cutting tip 422. After the trochar had been fully inserted at the desired location within the patient, control wire 414 would be activated to rotate imaging section 418 about micro hinge 416. Then, the desired surgical procedure could be conducted by inserting the appropriate surgical instruments through the trochar 400 while the surgical procedure is viewed by the imaging device. At the end of the surgical procedure, any surgical instruments inserted through entry trochar 400 would be removed, the imaging section 418 would be rotated back to its closed position, and the trochar 400 would be removed from within the body of the patient. It should be understood that the entry trochar 400 of this invention can be of a very small diameter. Typically, the diameter of the imaging section 418 and the cylindrical tube 402 would be in the range of 2–10 mm. Of course, the trochar diameter could be of a larger size, if necessary, to accommodate a surgical procedure which required the use of larger interventional instruments.

By the foregoing, it is apparent that many surgical procedures can be enhanced by the use of a very small microendoscope which provides an integral imaging capability to the surgeon, or the use of the imaging device directly incorporated into a device such as an entry trochar. Relatively large surgical instruments such as Jackson grasping forceps may be provided with their own integral imaging capability by the attachment of the microendoscope. The introduction of stents into arteries may now be achieved with direct view of the blockage by the microendoscope which is introduced simultaneously with the catheter. In procedures where tissue must be separated or dissected, very precise tissue manipulation can occur by use of an over-tube device which is placed directly over the microendoscope. In yet another application, the use of a balloon catheter may be enhanced by the microendoscope which is again introduced simultaneously with the catheter.

This invention has been described in detail with reference to particular embodiments thereof, but it will be understood that various other modifications can be effected within the spirit and scope of this invention.

What is claimed is:

1. A surgical device with removable imaging capability for use at a surgical site, said surgical device comprising:
    a microendoscope including an elongate tubular portion having a peripheral wall and a central passageway formed therethrough, an image sensor placed within said central passageway at a distal end of said tubular portion, said image sensor lying in a first plane and including an array of CMOS pixels for receiving images thereon, said image sensor further including circuitry means on said first plane and coupled to said array of CMOS pixels for timing and control of said array of CMOS pixels, said image sensor producing a pre-video signal;
    a control box remote from said image sensor, said control box including circuitry means for receiving said pre-video signal from said image sensor, and for converting said pre-video signal to a post-video signal which may be received by a standard video device;
    a power supply coupled to said control box and said image sensor for providing power thereto;
    grasping forceps including an instrument channel having a central opening formed therethrough, grasping tines having proximal ends connected to one another and distal ends spaced apart a desired distance, said proximal ends being inserted through said central opening, a first member having a distal end attached to said proximal ends of said grasping tines, a second member having a distal end attached to said instrument channel, said first member being movable with respect to said second member to move said grasping tines longitudinally within said instrument channel to cause said distal ends of said grasping tines to be pressed together when entering said central opening or to be spaced apart when exiting said central opening; and
    an endoscope tube attached exteriorly of said instrument channel for receiving said microendoscope such that said microendoscope may provide a visual image as said grasping forceps are manipulated within the body of a patient.

2. A device, as claimed in claim 1, further including:
    a lens within said passageway of said tubular portion to condition the image of the surgical site prior to being received by said image sensor.

3. A device, as claimed in claim 1, further including:
    a plurality of longitudinal channels formed within said peripheral wall of said elongate sheath; and
    at least one light fiber in one of said plurality of longitudinal channels and extending to said distal end of said tubular portion, said light fiber communicating with a source of light to illuminate the surgical area under observation.

4. A surgical device, as claimed in claim 1, wherein said control box further includes:
    a supplementary circuit board for digitally enhancing the pre-video signal, said supplementary circuit board coupled to said circuitry means for receiving said pre-video signal and for converting said pre-video signal.

5. A surgical device, as claimed in claim 1, wherein said array of CMOS pixels further includes:
    an array of passive CMOS pixels, wherein individual passive CMOS pixels of said array of passive CMOS pixels each includes a photo diode for producing photoelectrically generated signals; and
    an access transistor communicating with said photo diode to control the release of said photoelectrically generated signals.

6. A surgical device, as claimed in claim 1, wherein said array of CMOS pixels further includes:
    an array of active CMOS pixels, wherein individual active CMOS pixels within said array of active CMOS pixels each includes an amplifier.

7. A surgical device with removable imaging capability for use at a surgical site, said surgical device comprising:
    a microendoscope including an elongate tubular portion having a peripheral wall and a central passageway formed therethrough, an image sensor placed within said central passageway at a distal end of said tubular portion, said image sensor including an array of CMOS pixels defining a profile area and lying in a first plane, said array of CMOS pixels for receiving images thereon;

a circuit board longitudinally aligned with and electrically coupled to said array of CMOS pixels, said circuit board lying in a second plane which is offset from said first plane and substantially parallel to said first plane, said circuit board including timing and control means for controlling the release of information from said array of CMOS pixels, said timing and control means producing a pre-video signal;

a control box remote from said array of CMOS pixels and said circuit board, said control box including circuitry means for receiving said pre-video signal, and for converting said pre-video signal to a post-video signal which may be received by a standard video device;

a power supply coupled to said control box, said array of CMOS pixels and said timing and control means providing power thereto;

grasping forceps including an instrument channel having a central opening formed therethrough, grasping tines having proximal ends connected to one another and distal ends spaced apart a desired distance, said proximal ends being inserted through said central opening, a first member having a distal end attached to said proximal ends of said grasping tines, a second member having a distal end attached to said instrument channel, said first member being movable with respect to said second member to move said grasping tines longitudinally within said instrument channel to cause said distal ends of said grasping tines to be pressed together when entering said central opening or to be spaced apart when exiting said central opening; and an endoscope tube attached exteriorly of said instrument channel for receiving said microendoscope such that said microendoscope may provide a visual image as said grasping forceps are manipulated within the body of a patient.

8. A surgical device, as claimed in claim 7, wherein said control box further includes:

a supplementary circuit board for digitally enhancing the pre-video signal, said supplementary circuit board coupled to said circuitry means for receiving said pre-video signal and for converting said pre-video signal.

9. A surgical device, as claimed in claim 8, wherein said array of CMOS pixels further includes:

an array of passive CMOS pixels, wherein individual passive CMOS pixels of said array of passive CMOS pixels each includes a photo diode for producing photoelectrically generated signals; and an access transistor communicating with said photo diode to control the release of said photoelectrically generated signals.

10. A surgical device, as claimed in claim 8, wherein said array of CMOS pixels further includes:

an array of active CMOS pixels, wherein individual active CMOS pixels within said array of active CMOS pixels each includes an amplifier.

11. A surgical device with removal imaging capability for use at a surgical site, said surgical device comprising:

a microendoscope including an elongate tubular portion having a peripheral wall and a central passageway formed therethrough, an image sensor placed within said central passageway at a distal end of said tubular portion said image sensor lying in a first plane and including an array of CMOS pixels for receiving images thereon, said image sensor further including circuitry means on said first plane and coupled to said array of CMOS pixels for timing and control of said array of CMOS pixels, said image sensor producing a pre-video signal;

a control box remote from said image sensor, said control box including circuitry means for receiving said pre-video signal from said image sensor, and for converting said pre-video signal to a post-video signal which may be received by a standard video device;

a power supply coupled to said control box, said array of CMOS pixels and said timing and control means providing power thereto; and a stent placement catheter including a tube having a central opening formed therethrough, a stent coil positioned at a distal end of said tube and exteriorly thereof, at least one control wire connected to said stent coil, said at least one control wire extending longitudinally along said tube, said microendoscope being insertable through said central opening such that said microendoscope may provide a visual image as said catheter is manipulated within the body of a patient.

12. A device, as claimed in claim 11, further including:

a lens within said passageway of said elongate tubular portion to condition the image of the surgical site prior to being received by said image sensor.

13. A device, as claimed in claim 11, further including:

a plurality of longitudinal channels formed within said peripheral wall of said elongate tubular portion; and at least one light fiber in one of said plurality of longitudinal channels and extending to said distal end of said elongate tubular portion, said light fiber communicating with a source of light to illuminate the surgical area under observation.

14. A surgical device, as claimed in claim 11, wherein said control box further includes:

a supplementary circuit board for digitally enhancing the pre-video signal, said supplementary circuit board coupled to said circuitry means for receiving said pre-video signal and for converting said pre-video signal.

15. A surgical device, as claimed in claim 11, wherein said array of said CMOS pixels further includes:

an array of passive CMOS pixels, wherein individual passive CMOS pixels of said array of passive CMOS pixels each includes a photo diode for producing photoelectrically generated signals; and an access transistor communicating with said photo diode to control the release of said photoelectrically generated signals.

16. A surgical device, as claimed in claim 11, wherein said array of CMOS pixels further includes:

an array of active CMOS pixels, wherein individual active CMOS pixels within said array of active CMOS pixels each includes an amplifier.

17. A surgical device with removal imaging capability for use at a surgical site, said surgical device comprising:

a microendoscope including an elongate tubular portion having a peripheral wall and a central passageway formed therethrough, an image sensor placed within said central passageway at a distal end of said tubular portion, said image sensor including an array of CMOS pixels defining a profile area and lying in a first plane, said array of CMOS pixels for receiving images thereon;

a circuit board longitudinally aligned with and electrically coupled to said array of CMOS pixels, said circuit board lying in a second plane which is offset from said first plane and substantially parallel to said first plane, said circuit board including timing and control means for controlling the release of information from said array of CMOS pixels, said timing and control means producing a pre-video signal;

a control box remote from said array of CMOS pixels and said circuit board, said control box including circuitry means for receiving said pre-video signal, and for converting said pre-video signal to a post-video signal which may be received by a standard video device;

a power supply coupled to said control box, said array of CMOS pixels and said timing and control means providing power thereto; and a stent placement catheter including a tube having a central opening formed therethrough, a stent coil positioned at a distal end of said tube and exteriorly thereof, at least one control wire connected to said stent coil, said at least one control wire extending longitudinally along said tube, said microendoscope being insertable through said central opening such that said microendoscope may provide a visual image as said catheter is manipulated within the body of a patient.

18. A surgical device, as claimed in claim 17, wherein said control box further includes:

a supplementary circuit board for digitally enhancing the pre-video signal, said supplementary circuit board coupled to said circuitry means for receiving said pre-video signal and for converting said pre-video signal.

19. A surgical device, as claimed in claim 17, wherein said array of CMOS pixels further includes:

an array of passive CMOS pixels, wherein individual passive CMOS pixels of said array of passive CMOS pixels each includes a photo diode for producing photoelectrically generated signals; and an access transistor communicating with said photo diode to control the release of said photoelectrically generated signals.

20. A surgical device, as claimed in claim 17, wherein said array of CMOS pixels further includes:

an array of active CMOS pixels, wherein individual active CMOS pixels within said array of active CMOS pixels each includes an amplifier.

21. A surgical device with removable imaging capability for use at a surgical site, said surgical device comprising:

a microendoscope including an elongate tubular portion having a peripheral wall and a central passageway formed therethrough, an image sensor placed within said central passageway at a distal end of said tubular portion, said image sensor lying in a first plane and including an array of CMOS pixels for receiving images thereon, said image sensor further including circuitry means on said first plane and coupled to said array of CMOS pixels for timing and control of said array of CMOS pixels, said image sensor producing a pre-video signal;

a control box remote from said image sensor, said control box including circuitry means for receiving said pre-video signal from said image sensor, and for converting said pre-video signal to a post-video signal which may be received by a standard video device;

a power supply coupled to said control box and said image sensor for providing power thereto; and an over-tube device including a guide tube having a central opening formed therethrough, an extension connected to a distal end of said over-tube device and extending distally thereof, and a tissue contacting member attached to said extension for manipulating the tissue of a patient, said microendoscope being insertable through said central opening enabling said microendoscope to view said tissue contacting member and the surrounding surgical area as tissue manipulation occurs.

22. A device, as claimed in claim 21, further including:

a lens within said passageway of said elongate tubular portion to condition the image of the surgical site prior to being received by said image sensor.

23. A device, as claimed in claim 21, further including:

a plurality of longitudinal channels formed within said peripheral wall of said elongate tubular portion; and at least one light fiber in one of said plurality of longitudinal channels and extending to said distal end of said elongate tubular portion, said light fiber communicating with a source of light to illuminate the surgical area under observation.

24. A device, as claimed in claim 21, wherein said tissue contacting member is a separating bead having a spherical shape especially adapted for tissue separation.

25. A device, as claimed in claim 21, wherein said tissue contacting member is a hook-shaped structure enabling tissue cutting.

26. A surgical device, as claimed in claim 21, wherein said control box further includes:

a supplementary circuit board for digitally enhancing the pre-video signal, said supplementary circuit board coupled to said circuitry means for receiving said pre-video signal and for converting said pre-video signal.

27. A surgical device, as claimed in claim 21, wherein said array of CMOS pixels further includes:

an array of passive CMOS pixels, wherein individual passive CMOS pixels of said array of passive CMOS pixels each includes a photo diode for producing photoelectrically generated signals; and an access transistor communicating with said photo diode to control the release of said photoelectrically generated signals.

28. A surgical device, as claimed in claim 21, wherein said array of CMOS pixels further includes:

an array of active CMOS pixels, wherein individual active CMOS pixels within said array of active CMOS pixels each includes an amplifier.

29. A surgical device with removable imaging capability for use at a surgical site, said surgical device comprising:

a microendoscope including an elongate tubular portion having a peripheral wall and a central passageway formed therethrough, an image sensor placed within said central passageway at a distal end of said tubular portion, said image sensor including an array of CMOS pixels defining a profile area and lying in a first plane, said array of CMOS pixels for receiving images thereon;

a circuit board longitudinally aligned with and electrically coupled to said array of CMOS pixels, said circuit board lying in a second plane which is offset from said first plane and substantially parallel to said first plane, said circuit board including timing and control means for controlling the release of information from said array of CMOS pixels, said timing and control means producing a pre-video signal;

a control box remote from said array of CMOS pixels and said circuit board, said control box including circuitry means for receiving said pre-video signal, and for converting said pre-video signal to a post-video signal which may be received by a standard video device;

a power supply coupled to said control box and said image sensor for providing power thereto; and an over-tube device including a guide tube having a central opening formed therethrough, an extension connected to a distal end of said over-tube device and extending distally thereof, and a tissue contacting member attached to said extension for manipulating the tissue of a patient, said microendoscope being insertable through said central opening enabling said microendoscope to view said tissue contacting member and the surrounding surgical area as tissue manipulation occurs.

30. A surgical device, as claimed in claim 29, wherein said control box further includes:

a supplementary circuit board for digitally enhancing the pre-video signal, said supplementary circuit board coupled to said circuitry means for receiving said pre-video signal and for converting said pre-video signal.

31. A surgical device, as claimed in claim 29, wherein said array of CMOS pixels further includes:

an array of passive CMOS pixels, wherein individual passive CMOS pixels of said array of passive CMOS pixels each includes a photo diode for producing photoelectrically generated signals; and an access transistor communicating with said photo diode to control the release of said photoelectrically generated signals.

32. A surgical device, as claimed in claim 29, wherein said array of CMOS pixels further includes:

an array of active CMOS pixels, wherein individual active CMOS pixels within said array of active CMOS pixels each includes an amplifier.

33. A surgical device with removable imaging capability for use at a surgical site, said surgical device comprising:

a microendoscope including an elongate tubular portion having a peripheral wall and a central passageway formed therethrough, an image sensor placed within said central passageway at a distal end of said tubular portion, said image sensor lying in a first plane and including an array of CMOS pixels for receiving images thereon, said image sensor further including circuitry means on said first plane and coupled to said array of CMOS pixels for timing and control of said array of CMOS pixels, said image sensor producing a pre-video signal;

a control box remote from said image sensor, said control box including circuitry means for receiving said pre-video signal from said image sensor, and for converting said pre-video signal to a post-video signal which may be received by a standard video device;

a power supply coupled to said control box and said image sensor for providing power thereto; and a balloon catheter including a guide tube having a distal end, a periphery, and a central opening formed therethrough, a balloon attached around said distal end and said periphery of said guide tube, at least one hole formed through said distal end of said guide tube, means to introduce gas through said at least one hole, said introducing means communicating with a source of air to inflate said balloon, wherein said microendoscope is insertable through said central opening to enable the microendoscope to provide a visual image as said balloon catheter is manipulated within the body of a patient.

34. A device, as claimed in claim 33, further including:

a lens within said passageway of said elongate tubular portion to condition the image of the surgical site prior to being received by said image sensor.

35. A device, as claimed in claim 33, further including:

a plurality of longitudinal channels formed within said peripheral wall of said elongate tubular portion; and at least one light fiber in one of said plurality of longitudinal channels and extending to said distal end of said elongate tubular portion, said light fiber communicating with a source of light to illuminate the surgical area under observation.

36. A device, as claimed in claim 33, further including:

a stop cock placed in line with said introducing means to control flow of air through said holes.

37. A surgical device, as claimed in claim 33, wherein said control box further includes:

a supplementary circuit board for digitally enhancing the pre-video signal, said supplementary circuit board coupled to said circuitry means for receiving said pre-video signal and for converting said pre-video signal.

38. A surgical device, as claimed in claim 33, wherein said array of CMOS pixels further includes:

an array of passive CMOS pixels, wherein individual passive CMOS pixels of said array of passive CMOS pixels each includes a photo diode for producing photoelectrically generated signals; and an access transistor communicating with said photo diode to control the release of said photoelectrically generated signals.

39. A surgical device, as claimed in claim 33, wherein said array of CMOS pixels further includes:

an array of active CMOS pixels, wherein individual active CMOS pixels within said array of active CMOS pixels each includes an amplifier.

40. A surgical device with removable imaging capability for use at a surgical site, said surgical device comprising:

a microendoscope including an elongate tubular portion having a peripheral wall and a central passageway formed therethrough, an image sensor placed within said central passageway at a distal end of said tubular portion, said image sensor including an array of CMOS pixels defining a profile area and lying in a first plane, said array of CMOS pixels for receiving images thereon;

a circuit board longitudinally aligned with and electrically coupled to said array of CMOS pixels, said circuit board lying in a second plane which is offset from said first plane and substantially parallel to said first plane, said circuit board including timing and control means for controlling the release of information from said array of CMOS pixels, said timing and control means producing a pre-video signal;

a control box remote from said array of CMOS pixels and said circuit board, said control box including circuitry means for receiving said pre-video signal, and for converting said pre-video signal to a post-video signal which may be received by a standard video device;

a power supply coupled to said control box, said array of CMOS pixels and said timing and control means providing power thereto; and a balloon catheter including a guide tube having a distal end, a periphery, and a central opening formed therethrough, a balloon attached around said distal end and said periphery of said guide tube, at least one hole formed through said distal end of said guide tube, a means to introduce gas through said at least one hole, said introducing means communicating with a source of air to inflate said balloon, wherein said microendoscope is insertable through said central opening to enable the microendoscope to provide a visual image as said balloon catheter is manipulated within the body of a patient.

41. A surgical device, as claimed in claim 40, wherein said control box further includes:

a supplementary circuit board for digitally enhancing the pre-video signal, said supplementary circuit board coupled to said circuitry means for receiving said pre-video signal and for converting said pre-video signal.

42. A surgical device, as claimed in claim 40, wherein said array of CMOS pixels further includes:

an array of passive CMOS pixels, wherein individual passive CMOS pixels of said array of passive CMOS pixels each includes a photo diode for producing photoelectrically generated signals; and an access transistor communicating with said photo diode to control the release of said photoelectrically generated signals.

43. A surgical device, as claimed in claim 40, wherein said array of CMOS pixels further includes:

an array of active CMOS pixels, wherein individual active CMOS pixels within said array of active CMOS pixels each includes an amplifier.

44. A surgical device with removable imaging capability for use at a surgical site, said device comprising:

a microendoscope including an elongate tubular portion having a peripheral wall and a central passageway formed therethrough, an image sensor placed within said central passageway at a distal end of said tubular portion, said image sensor lying in a first plane and including an array of CMOS pixels for receiving images thereon, said image sensor further including circuitry means on said first plane and coupled to said array of CMOS pixels for timing and control of said array of CMOS pixels, said image sensor producing a pre-video signal;

a control box remote from said image sensor, said control box including circuitry means for receiving said pre-video signal from said image sensor, and for converting said pre-video signal to a post-video signal which may be received by a standard video device;

a power supply coupled to said control box and said image sensor for providing power thereto; and an endotracheal intubation assembly including an endotracheal tube having an open distal end, an inflatable balloon surrounding said endotracheal tube near said distal end thereof, and means communicating with said inflatable balloon for selective inflation of said inflatable balloon, a centering tube removably inserted through said endotracheal tube, said centering tube having a distal end positioned adjacent said open distal end of said endotracheal tube, wherein said microendoscope is removably inserted through said centering tube to enable said microendoscope to provide a visual image as said endotracheal tube is manipulated to intubate a patient.

45. A device, as claimed in claim 44, wherein said centering tube further includes:

a plurality of peripheral channels formed in said centering tube and extending along the length thereof, said plurality of peripheral channels allowing fluid or gas to be introduced therethrough.

46. A surgical device, as claimed in claim 44, wherein said control box further includes:

a supplementary circuit board for digitally enhancing the pre-video signal, said supplementary circuit board coupled to said circuitry means for receiving said pre-video signal and for converting said pre-video signal.

47. A surgical device, as claimed in claim 44, wherein said array of CMOS pixels further includes:

an array of passive CMOS pixels, wherein individual passive CMOS pixels of said array of passive CMOS pixels each includes a photo diode for producing photoelectrically generated signals; and an access transistor communicating with said photo diode to control the release of said photoelectrically generated signals.

48. A surgical device, as claimed in claim 1, wherein said array of CMOS pixels further includes:

an array of active CMOS pixels, wherein individual active CMOS pixels within said array of active CMOS pixels each includes an amplifier.

49. A surgical device in the form of an entry trochar with integral imaging capability for use at a surgical site, said surgical device comprising:

a cylindrical tube having a proximal end and a distal end;

an entry port connected to said proximal end of said cylindrical tube allowing surgical instruments to be placed through said cylindrical tube for performing surgical procedures at the surgical site;

an imaging section connected to said distal end of said cylindrical tube and having a viewing end for viewing the surgical site, said imaging section having an image sensor mounted within said imaging section, said image sensor lying in a first plane and including an array of CMOS pixels for receiving images thereon, said image sensor further including circuitry means on said first plane and coupled to said array of CMOS pixels for timing and control of said array of CMOS pixels, said image sensor producing a pre-video signal;

means mounted to said cylindrical tube for rotating the imaging section to expose said viewing end to the surgical site;

a control box remote from said image sensor, said control box including circuitry means for receiving said pre-video signal from said image sensor, and for converting said pre-video signal to a post-video signal which may be received by a standard video device; and a power supply coupled to said control box and said image sensor for providing power thereto.

50. A device, as claimed in claim 49, further including:

a lens mounted to said viewing end of said imaging section to condition an image prior to being received by said image sensor.

51. A device, as claimed in claim 49, further including:

a light source mounted within said imaging section; and a plurality of light fibers mounted within said imaging section, communicating with said light source and extending toward said viewing end of said imaging section for providing a distributed light source to the surgical site.

52. A device, as claimed in claim 49, wherein said control box further includes:

a supplementary circuit board for digitally enhancing the pre-video signal, said supplementary circuit board coupled to said circuitry means for receiving said pre-video signal and for converting said pre-video signal.

53. A device, as claimed in claim 49, wherein said array of CMOS pixels further includes:

an array of passive CMOS pixels, wherein individual passive CMOS pixels of said array of said passive CMOS pixels each includes a photo diode for producing photoelectrically generated signals; and an access transistor communicating with said photo diode to control the release of said photoelectrically generated signals.

54. A surgical device, as claimed in claim 49, wherein said array of CMOS pixels further includes:

an array of active CMOS pixels, wherein individual active CMOS pixels within said array of active CMOS pixels each includes an amplifier.

55. A surgical device in the form of an entry trochar with integral imaging capability for use at a surgical site, said surgical device comprising:

a cylindrical tube having a proximal end and a distal end;

an entry port connected to said proximal end of said cylindrical tube allowing surgical instruments to be placed through said cylindrical tube for performing surgical procedures at the surgical site;

an imaging section connected to said distal end of said cylindrical tube and having a viewing end for viewing of the surgical site, said imaging section having an image sensor mounted within said imaging section, said image sensor including an array of CMOS pixels defining a profile area and lying in a first plane, said array of CMOS pixels for receiving images thereon;

a circuit board longitudinally aligned with and electrically coupled to said array of CMOS pixels, said circuit board lying in a second plane which is spaced from said first plane and substantially parallel to said first plane, said circuit board including timing and control means for controlling the release of information from said array of CMOS pixels, said timing and control means producing a pre-video signal;

a control box remote from said array of CMOS pixels and said circuit board, said control box including circuitry means for receiving said pre-video signal, and for converting said pre-video signal to a post-video signal which may be received by a standard video device;

a power supply coupled to said control box, said array of CMOS pixels and said timing and control means providing power thereto; and means mounted to said cylindrical tube for rotating the imaging section to expose said viewing end to the surgical site.

56. A surgical device, as claimed in claim 55, wherein said control box further includes:

a supplementary circuit board for digitally enhancing the pre-video signal, said supplementary circuit board coupled to said circuitry means for receiving said pre-video signal and for converting said pre-video signal.

57. A surgical device, as claimed in claim 55, wherein said array of CMOS pixels further includes:

an array of passive CMOS pixels, wherein individual passive CMOS pixels of said array of passive CMOS pixels each includes a photo diode for producing photoelectrically generated signals; and an access transistor communicating with said photo diode to control the release of said photoelectrically generated signals.

58. A surgical device, as claimed in claim 55, wherein said array of CMOS pixels further includes:

an array of active CMOS pixels, wherein individual active CMOS pixels within said array of active CMOS pixels each includes an amplifier.

* * * * *